United States Patent
Hebert et al.

(10) Patent No.: US 11,096,679 B2
(45) Date of Patent: *Aug. 24, 2021

(54) MICROGRAFT FOR THE TREATMENT OF INTRACRANIAL ANEURYSMS AND METHOD FOR USE

(71) Applicant: Neurogami Medical, Inc., Mountain View, CA (US)

(72) Inventors: Stephen J. Hebert, San Francisco, CA (US); Bartosz Bojanowski, San Francisco, CA (US)

(73) Assignee: Neurogami Medical, Inc., Mountain View, CA (US)

( * ) Notice: Subject to any disclaimer, the term of this patent is extended or adjusted under 35 U.S.C. 154(b) by 228 days.

This patent is subject to a terminal disclaimer.

(21) Appl. No.: 16/409,742

(22) Filed: May 10, 2019

(65) Prior Publication Data

US 2019/0261967 A1 Aug. 29, 2019

Related U.S. Application Data

(63) Continuation of application No. 15/382,731, filed on Dec. 18, 2016, now Pat. No. 10,285,678, which is a
(Continued)

(51) Int. Cl.
*A61B 17/00* (2006.01)
*A61B 17/12* (2006.01)
(Continued)

(52) U.S. Cl.
CPC ...... *A61B 17/0057* (2013.01); *A61B 17/1214* (2013.01); *A61B 17/1215* (2013.01);
(Continued)

(58) Field of Classification Search
CPC .......... A61B 17/0057; A61B 17/12031; A61B 17/12113; A61B 17/12118;
(Continued)

(56) References Cited

U.S. PATENT DOCUMENTS 4,994,069 A 2/1991 Ritchart et al.
5,122,136 A 6/1992 Gugliemi et al.
(Continued)

FOREIGN PATENT DOCUMENTS

CN 1671330 9/2005
CN 203885554 U 10/2014
(Continued)

OTHER PUBLICATIONS

International Search Report and Written Opinion dated May 22, 2020 for International Application No. PCT/US2020/012361.
(Continued)

*Primary Examiner* — Katrina M Stransky
(74) *Attorney, Agent, or Firm* — Neil D. Gershon

(57) ABSTRACT

A device for occluding a vasculature of a patient including a micrograft having an absorbent polymeric structure with a lumen of transporting blood. The micrograft has a series of peaks and valleys formed by crimping. The occluding device is sufficiently small and flexible to be tracked on a guidewire and/or pushed through a microcatheter to a site within the vasculature of the patient. Delivery systems for delivering the micrografts are also disclosed.

19 Claims, 13 Drawing Sheets

Related U.S. Application Data continuation of application No. 14/997,008, filed on Jan. 15, 2016, now Pat. No. 9,999,413.

(60) Provisional application No. 62/105,648, filed on Jan. 20, 2015.

(51) Int. Cl.
    *A61F 2/06*     (2013.01)
    *A61F 2/07*     (2013.01)
    *A61B 90/00*     (2016.01)
    *A61F 2/95*     (2013.01)
    *B29D 23/00*     (2006.01)
    *B29D 23/18*     (2006.01)
    *B29K 67/00*     (2006.01)
    *B29K 105/00*     (2006.01)

(52) U.S. Cl.
CPC .. *A61B 17/12031* (2013.01); *A61B 17/12113* (2013.01); *A61B 17/12118* (2013.01); *A61B 17/12145* (2013.01); *A61B 17/12154* (2013.01); *A61B 17/12172* (2013.01); *A61B 17/12177* (2013.01); *A61F 2/06* (2013.01); *A61F 2/07* (2013.01); *B29D 23/00* (2013.01); *B29D 23/18* (2013.01); *A61B 2017/0053* (2013.01); *A61B 2017/00526* (2013.01); *A61B 2017/00778* (2013.01); *A61B 2017/00867* (2013.01); *A61B 2017/00893* (2013.01); *A61B 2017/00898* (2013.01); *A61B 2017/00942* (2013.01); *A61B 2017/1205* (2013.01); *A61B 2017/12054* (2013.01); *A61B 2090/0807* (2016.02); *A61B 2090/3966* (2016.02); *A61F 2/95* (2013.01); *A61F 2002/077* (2013.01); *B29K 2067/003* (2013.01); *B29K 2105/0035* (2013.01); *B29K 2105/25* (2013.01)

(58) Field of Classification Search
CPC .......... A61B 17/1214; A61B 17/12145; A61B 17/1215; A61B 17/12154; A61B 17/12172; A61B 17/12177; A61F 2/06; A61F 2/07

See application file for complete search history.

(56) References Cited

U.S. PATENT DOCUMENTS

| | | | |
|---|---|---|---|
| 5,226,911 A | 7/1993 | Chee et al. | |
| 5,234,437 A | 8/1993 | Sepetka | |
| 5,250,071 A | 10/1993 | Palermo | |
| 5,261,916 A | 11/1993 | Engelson | |
| 5,304,195 A | 4/1994 | Twyford, Jr. | |
| 5,350,397 A | 9/1994 | Palermo | |
| 5,354,295 A | 10/1994 | Gugliemi et al. | |
| 5,382,259 A * | 1/1995 | Phelps | A61B 17/1215 606/151 |
| 5,423,849 A | 6/1995 | Engelson et al. | |
| 5,522,836 A | 6/1996 | Palermo | |
| 5,645,558 A | 7/1997 | Horton | |
| 5,690,666 A * | 11/1997 | Berenstein | A61B 17/12022 606/191 |
| 5,743,905 A | 4/1998 | Eder et al. | |
| 5,826,587 A | 10/1998 | Berenstein et al. | |
| 5,895,391 A | 4/1999 | Farnholtz | |
| 5,911,731 A | 6/1999 | Pham et al. | |
| 5,935,145 A | 8/1999 | Villar et al. | |
| 5,935,148 A | 8/1999 | Villar et al. | |
| 5,944,733 A | 8/1999 | Engelson | |
| 5,964,797 A | 10/1999 | Ho | |
| 5,984,929 A | 11/1999 | Bashiri et al. | |
| 6,059,779 A | 5/2000 | Mills | |
| 6,063,070 A | 5/2000 | Eder | |
| 6,096,034 A | 8/2000 | Kupiecki | |
| 6,136,015 A | 10/2000 | Kurz et al. | |
| 6,156,061 A | 12/2000 | Wallace et al. | |
| 6,159,165 A | 12/2000 | Ferrera et al. | |
| 6,165,178 A | 12/2000 | Bashiri et al. | |
| 6,168,615 B1 | 1/2001 | Ken et al. | |
| 6,171,326 B1 | 1/2001 | Ferrera et al. | |
| 6,193,708 B1 | 2/2001 | Ken et al. | |
| 6,231,586 B1 | 5/2001 | Mariant | |
| 6,238,415 B1 | 5/2001 | Sepetka et al. | |
| 6,254,592 B1 | 7/2001 | Samson et al. | |
| 6,280,457 B1 | 8/2001 | Wallace et al. | |
| 6,287,318 B1 | 9/2001 | Villar et al. | |
| 6,296,622 B1 | 10/2001 | Kurz et al. | |
| 6,299,627 B1 | 10/2001 | Eder et al. | |
| 6,306,153 B1 | 10/2001 | Kurz et al. | |
| 6,309,367 B1 | 10/2001 | Boock | |
| 6,312,421 B1 | 11/2001 | Boock | |
| 6,371,972 B1 | 4/2002 | Wallace et al. | |
| 6,375,668 B1 | 4/2002 | Gifford | |
| 6,375,669 B1 | 4/2002 | Rosenbluth et al. | |
| 6,383,204 B1 | 5/2002 | Ferrera et al. | |
| 6,409,721 B1 | 6/2002 | Wheelock et al. | |
| 6,425,914 B1 | 7/2002 | Wallace et al. | |
| 6,454,780 B1 | 9/2002 | Wallace | |
| 6,458,119 B1 | 10/2002 | Berenstein et al. | |
| 6,475,169 B2 | 11/2002 | Ferrera | |
| 6,544,275 B1 | 4/2003 | Teoh | |
| 6,551,305 B2 | 4/2003 | Ferrera et al. | |
| 6,585,754 B2 | 7/2003 | Wallace et al. | |
| 6,589,230 B2 | 7/2003 | Gia et al. | |
| 6,605,101 B1 | 8/2003 | Schaefer et al. | |
| 6,623,493 B2 | 9/2003 | Wallace et al. | |
| 6,626,928 B1 | 9/2003 | Raymond et al. | |
| 6,660,020 B2 | 12/2003 | Wallace | |
| 6,679,903 B2 | 1/2004 | Kurz | |
| 6,716,223 B2 | 4/2004 | Leopold et al. | |
| 6,746,475 B1 | 6/2004 | Rivelli, Jr. | |
| 6,786,876 B2 | 9/2004 | Cox | |
| 6,802,851 B2 | 10/2004 | Jones et al. | |
| 6,872,218 B2 | 3/2005 | Ferrera | |
| 6,913,618 B2 | 7/2005 | Denardo et al. | |
| 6,929,654 B2 | 8/2005 | Teoh et al. | |
| 7,070,608 B2 | 7/2006 | Kurz et al. | |
| 7,083,632 B2 | 8/2006 | Avellanet et al. | |
| 7,201,768 B2 | 4/2007 | Diaz | |
| 7,232,461 B2 | 6/2007 | Ramer | |
| 7,241,301 B2 | 7/2007 | Thramann et al. | |
| 7,316,701 B2 | 1/2008 | Ferrera et al. | |
| 7,326,225 B2 | 2/2008 | Ferrera et al. | |
| 7,410,482 B2 | 8/2008 | Murphy et al. | |
| 7,442,382 B2 | 10/2008 | Henson et al. | |
| 7,488,332 B2 | 2/2009 | Teoh et al. | |
| 7,494,687 B2 | 2/2009 | Cox | |
| 7,599,933 B2 | 7/2009 | Wallace et al. | |
| 7,569,626 B2 | 8/2009 | Truckai | |
| 7,572,288 B2 | 8/2009 | Cox | |
| 7,608,088 B2 | 10/2009 | Jones | |
| 7,678,135 B2 | 3/2010 | Maahs | |
| 7,695,484 B2 | 4/2010 | Wallace et al. | |
| 7,695,488 B2 | 4/2010 | Berenstein | |
| 7,708,754 B2 | 5/2010 | Balgobin | |
| 7,708,755 B2 | 5/2010 | David | |
| 7,740,637 B2 | 6/2010 | Gandhi et al. | |
| 7,780,680 B2 | 8/2010 | Gandhi et al. | |
| 7,842,054 B2 | 11/2010 | Greene, Jr. et al. | |
| 7,842,068 B2 | 11/2010 | Ginn | |
| 8,002,789 B2 | 8/2011 | Ramzipoor et al. | |
| 8,016,852 B2 | 9/2011 | Ho et al. | |
| 8,034,075 B2 | 10/2011 | Dehnad | |
| 8,142,456 B2 | 3/2012 | Rosqueta et al. | |
| 8,172,862 B2 | 5/2012 | Wallace et al. | |
| 8,182,506 B2 | 5/2012 | Fitz et al. | |
| 8,221,483 B2 | 7/2012 | Ford et al. | |
| 8,257,394 B2 | 9/2012 | Saadat | |
| 8,267,923 B2 | 9/2012 | Murphy et al. | |
| 8,267,955 B2 | 9/2012 | Patterson et al. | |
| 8,273,100 B2 | 9/2012 | Martinez | |
| 8,292,914 B2 | 10/2012 | Morsi | |

(56) References Cited

U.S. PATENT DOCUMENTS

| | | |
|---|---|---|
| 8,298,256 B2 | 10/2012 | Gandhi et al. |
| 8,333,796 B2 | 12/2012 | Tompkins |
| 8,361,104 B2 | 1/2013 | Jones et al. |
| 8,361,138 B2 | 1/2013 | Adams |
| 8,376,996 B2 | 2/2013 | Wilson et al. |
| 8,398,701 B2 | 3/2013 | Berez et al. |
| 8,425,548 B2 | 4/2013 | Conner |
| 8,439,871 B2 | 5/2013 | Wilson et al. |
| 8,444,668 B2 | 5/2013 | Jones |
| 8,470,013 B2 | 6/2013 | Duggal et al. |
| 8,486,101 B2 | 7/2013 | Tran et al. |
| 8,535,345 B2 | 9/2013 | Desai et al. |
| 8,540,671 B2 | 9/2013 | Wilson et al. |
| 8,545,530 B2 | 10/2013 | Eskridge et al. |
| 8,597,320 B2 | 12/2013 | Sepetka et al. |
| 8,608,772 B2 | 12/2013 | Wilson et al. |
| 8,657,816 B2 | 2/2014 | Truckai |
| 8,715,312 B2 | 5/2014 | Burke et al. |
| 8,715,316 B1 | 5/2014 | Janardhan et al. |
| 8,764,788 B2 | 7/2014 | Martinez |
| 8,771,265 B2 | 7/2014 | Truckai |
| 8,771,294 B2 | 7/2014 | Sepetka et al. |
| 8,777,979 B2 | 7/2014 | Shrivastava |
| 8,795,316 B2 | 8/2014 | Balgobin |
| 8,801,747 B2 | 8/2014 | Stauss et al. |
| 8,833,224 B2 | 9/2014 | Thompson et al. |
| 8,876,855 B2 | 11/2014 | Plaza et al. |
| 8,888,806 B2 | 11/2014 | Desai et al. |
| 8,926,650 B2 | 1/2015 | Que |
| 8,932,317 B2 | 1/2015 | Marks et al. |
| 8,998,947 B2 | 4/2015 | Aboytes et al. |
| 9,011,480 B2 | 4/2015 | Divino et al. |
| 9,011,482 B2 | 4/2015 | Wallace et al. |
| 9,060,777 B1 | 6/2015 | Wallace et al. |
| 9,186,151 B2 | 11/2015 | Tompkins et al. |
| 9,192,389 B2 | 11/2015 | Tekulve |
| 9,295,473 B2 | 3/2016 | Hewitt et al. |
| 9,301,764 B2 | 4/2016 | White, Jr. et al. |
| 9,314,326 B2 | 4/2016 | Wallace et al. |
| 9,451,963 B2 | 9/2016 | Cruise et al. |
| 9,561,121 B2 | 2/2017 | Sudin et al. |
| 9,572,694 B2 | 2/2017 | Caro et al. |
| 9,579,104 B2 | 2/2017 | Beckham et al. |
| 9,592,068 B2 | 3/2017 | Janardham et al. |
| 9,615,832 B2 | 4/2017 | Bose et al. |
| 9,687,245 B2 | 6/2017 | Molaei et al. |
| 9,763,667 B2 | 9/2017 | Fercik Grant et al. |
| 9,775,494 B2 | 10/2017 | Takasugi |
| 9,775,590 B2 | 10/2017 | Ryan et al. |
| 9,855,052 B2 | 1/2018 | Aboytes et al. |
| 9,867,622 B2 | 1/2018 | Bowman |
| 9,907,556 B2 | 3/2018 | Truckai |
| 9,907,557 B2 | 3/2018 | Wallace et al. |
| 9,962,146 B2 | 5/2018 | Hebert |
| 9,968,360 B2 | 5/2018 | Stoppenhagen |
| 9,974,544 B2 | 5/2018 | Tekulve |
| 9,999,413 B2* | 6/2018 | Hebert .............. A61B 17/12118 |
| 10,064,627 B2 | 9/2018 | Aboytes et al. |
| 10,159,490 B2 | 12/2018 | Wallace et al. |
| 10,182,822 B2 | 1/2019 | Freudenthal |
| 10,231,722 B2 | 3/2019 | Hebert |
| 10,285,678 B2 | 5/2019 | Hebert |
| 10,285,679 B2* | 5/2019 | Hebert ................ A61B 17/1214 |
| 10,299,799 B1 | 5/2019 | DeMeritt |
| 10,335,154 B2 | 7/2019 | Johnson et al. |
| 10,736,730 B2 | 8/2020 | Hebert |
| 2002/0002382 A1 | 1/2002 | Wallace et al. |
| 2002/0120276 A1 | 8/2002 | Greene |
| 2002/0128671 A1 | 9/2002 | Wallace et al. |
| 2003/0004533 A1 | 1/2003 | Dieck et al. |
| 2003/0004568 A1 | 1/2003 | Ken et al. |
| 2003/0093111 A1* | 5/2003 | Ken ................. A61B 17/12145<br>606/200 |
| 2003/0204246 A1 | 10/2003 | Chu |
| 2004/0059407 A1 | 3/2004 | Escamilla |
| 2004/0098028 A1* | 5/2004 | Martinez ............ A61B 17/1215<br>606/200 |
| 2005/0171572 A1 | 8/2005 | Martinez |
| 2005/0192621 A1 | 9/2005 | Wallace et al. |
| 2005/0251160 A1 | 11/2005 | Saadat |
| 2005/0277978 A1 | 12/2005 | Greenhalgh |
| 2005/0283182 A1 | 12/2005 | Pierce |
| 2006/0106421 A1 | 5/2006 | Teoh |
| 2006/0116713 A1 | 6/2006 | Sepetka et al. |
| 2006/0135986 A1 | 6/2006 | Wallace et al. |
| 2006/0155324 A1 | 7/2006 | Porter et al. |
| 2006/0200234 A1 | 9/2006 | Hines |
| 2006/0276823 A1 | 12/2006 | Mitelberg |
| 2006/0276824 A1 | 12/2006 | Mitelberg |
| 2006/0276828 A1 | 12/2006 | Balgobin |
| 2006/0276829 A1 | 12/2006 | Balgobin |
| 2006/0276830 A1 | 12/2006 | Balgobin |
| 2006/0276831 A1 | 12/2006 | Porter et al. |
| 2006/0276832 A1 | 12/2006 | Balgobin |
| 2006/0276833 A1 | 12/2006 | Balgobin |
| 2006/0276834 A1 | 12/2006 | Balgobin |
| 2007/0010849 A1 | 1/2007 | Balgobin |
| 2007/0010850 A1 | 1/2007 | Balgobin |
| 2007/0016233 A1 | 1/2007 | Ferrera et al. |
| 2007/0078479 A1* | 4/2007 | Belenkaya ........ A61B 17/12113<br>606/200 |
| 2007/0118172 A1 | 5/2007 | Balgobin |
| 2007/0186933 A1 | 8/2007 | Domingo |
| 2007/0225634 A1 | 9/2007 | Ferren |
| 2007/0293932 A1 | 12/2007 | Zilla |
| 2008/0045997 A1 | 2/2008 | Balgobin et al. |
| 2008/0082176 A1 | 4/2008 | Slazas |
| 2008/0097508 A1* | 4/2008 | Jones ................ A61B 17/12172<br>606/191 |
| 2008/0109057 A1 | 5/2008 | Calabria |
| 2008/0119887 A1 | 5/2008 | Que |
| 2008/0140177 A1 | 6/2008 | Hines |
| 2008/0269675 A1 | 10/2008 | Balgobin |
| 2008/0293932 A1 | 11/2008 | Wu et al. |
| 2008/0294237 A1 | 11/2008 | Chu |
| 2008/0300616 A1 | 12/2008 | Que et al. |
| 2009/0112251 A1* | 4/2009 | Qian ................ A61B 17/12163<br>606/194 |
| 2009/0227976 A1 | 9/2009 | Calabria |
| 2009/0297582 A1 | 12/2009 | Meyer et al. |
| 2009/0318941 A1 | 12/2009 | Sepetka et al. |
| 2009/0318948 A1 | 12/2009 | Linder |
| 2010/0268204 A1 | 10/2010 | Tieu |
| 2011/0125185 A1 | 5/2011 | Stopek et al. |
| 2011/0295303 A1* | 12/2011 | Freudenthal ..... A61B 17/12022<br>606/200 |
| 2012/0041472 A1 | 2/2012 | Tan |
| 2012/0158034 A1 | 6/2012 | Wilson |
| 2013/0072959 A1 | 3/2013 | Wu et al. |
| 2013/0138136 A1 | 5/2013 | Beckham |
| 2013/0245667 A1 | 9/2013 | Marchand et al. |
| 2013/0253572 A1* | 9/2013 | Molaei ............. A61B 17/12022<br>606/200 |
| 2013/0261657 A1 | 10/2013 | Lorenzo |
| 2013/0296917 A1 | 11/2013 | Rees et al. |
| 2014/0052233 A1 | 2/2014 | Cox et al. |
| 2014/0058434 A1 | 2/2014 | Jones |
| 2014/0257363 A1 | 9/2014 | Lippert |
| 2014/0288588 A1 | 9/2014 | Lam |
| 2014/0330299 A1 | 11/2014 | Rosenbluth et al. |
| 2015/0196304 A1 | 7/2015 | Rabkin et al. |
| 2015/0209050 A1 | 7/2015 | Aboytes et al. |
| 2015/0272589 A1 | 10/2015 | Lorenzo |
| 2015/0272590 A1 | 10/2015 | Aboytes et al. |
| 2015/0313605 A1 | 11/2015 | Griffin |
| 2015/0327976 A1 | 11/2015 | Divino et al. |
| 2015/0342613 A1 | 12/2015 | Aboytes et al. |
| 2016/0022445 A1 | 1/2016 | Ruvalcaba et al. |
| 2016/0206323 A1 | 7/2016 | Hebert et al. |
| 2016/0228123 A1 | 8/2016 | Anderson |
| 2016/0324528 A1 | 11/2016 | Hebert et al. |
| 2016/0324668 A1 | 11/2016 | Wallace et al. |
| 2017/0035430 A1 | 2/2017 | Sarge et al. |
| 2017/0035437 A1 | 2/2017 | Sarge et al. |

(56) References Cited

U.S. PATENT DOCUMENTS

| | | |
|---|---|---|
| 2017/0164951 A1 | 6/2017 | Divino et al. |
| 2017/0231789 A1 | 8/2017 | Cam et al. |
| 2018/0125501 A1 | 5/2018 | Aboytes et al. |
| 2018/0132859 A1 | 5/2018 | Aboytes et al. |
| 2018/0214159 A1 | 8/2018 | Zhang et al. |
| 2018/0221030 A1 | 8/2018 | Nita et al. |
| 2018/0289375 A1 | 10/2018 | Hebert et al. |
| 2018/0317933 A1 | 11/2018 | Nita et al. |
| 2019/0046211 A1 | 2/2019 | Bronikowski et al. |
| 2019/0201000 A1 | 7/2019 | Wallace et al. |
| 2019/0231362 A1 | 8/2019 | Maitland et al. |
| 2019/0314033 A1 | 10/2019 | Mirigian et al. |
| 2019/0374227 A1 | 12/2019 | Johnson et al. |
| 2019/0374228 A1 | 12/2019 | Wallace et al. |
| 2019/0374232 A1 | 12/2019 | Lorenzo |
| 2020/0000477 A1 | 1/2020 | Nita et al. |
| 2020/0038031 A1 | 2/2020 | Gorochow |

FOREIGN PATENT DOCUMENTS

| | | |
|---|---|---|
| WO | WO 94/09705 | 5/1994 |
| WO | WO 03/037191 | 5/2003 |
| WO | 2004/004580 | 1/2004 |
| WO | WO 2004/004580 | 1/2004 |
| WO | 2004/010878 | 2/2004 |
| WO | WO 2004/069059 | 8/2004 |
| WO | 2006/034149 | 3/2006 |
| WO | WO 2006/088531 | 8/2006 |
| WO | WO 2012/135859 | 10/2012 |
| WO | WO 2013/119332 | 8/2013 |
| WO | WO 2016/034149 | 3/2016 |
| WO | WO 2016/044188 | 3/2016 |
| WO | 2017/041554 | 3/2017 |
| WO | 2017/044982 | 3/2017 |
| WO | 2017/096188 | 6/2017 |
| WO | 2017/106265 | 6/2017 |
| WO | 2018/022954 | 2/2018 |
| WO | 2018/053314 | 3/2018 |
| WO | WO 2018/051187 | 3/2018 |
| WO | 2018/156833 | 8/2018 |
| WO | 2019/033978 | 2/2019 |

OTHER PUBLICATIONS

International Search Report and Written Opinion dated May 3, 2016 for International Application No. PCT/US2016/013638.

* cited by examiner

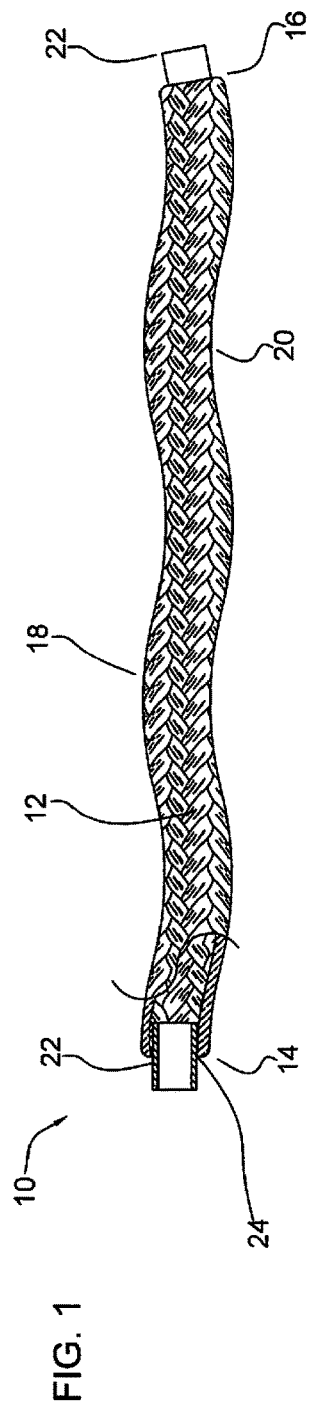
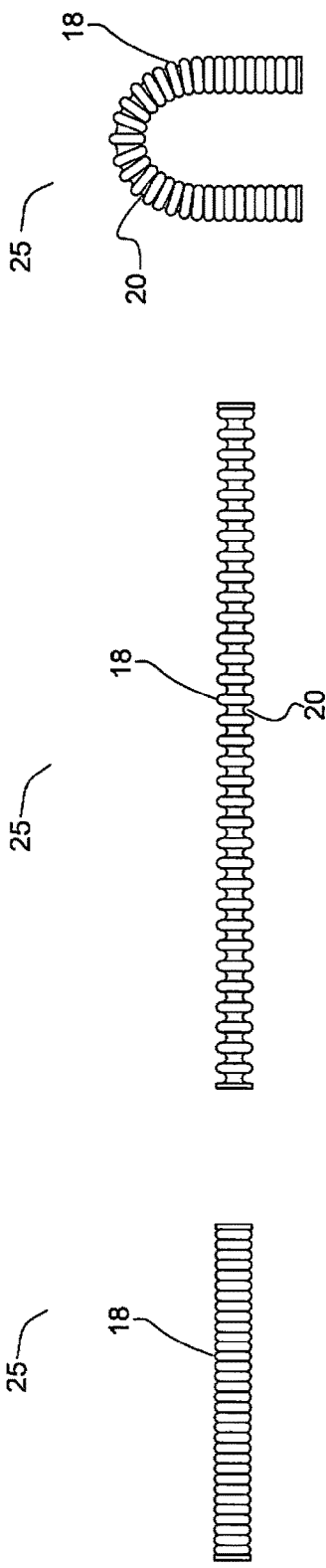
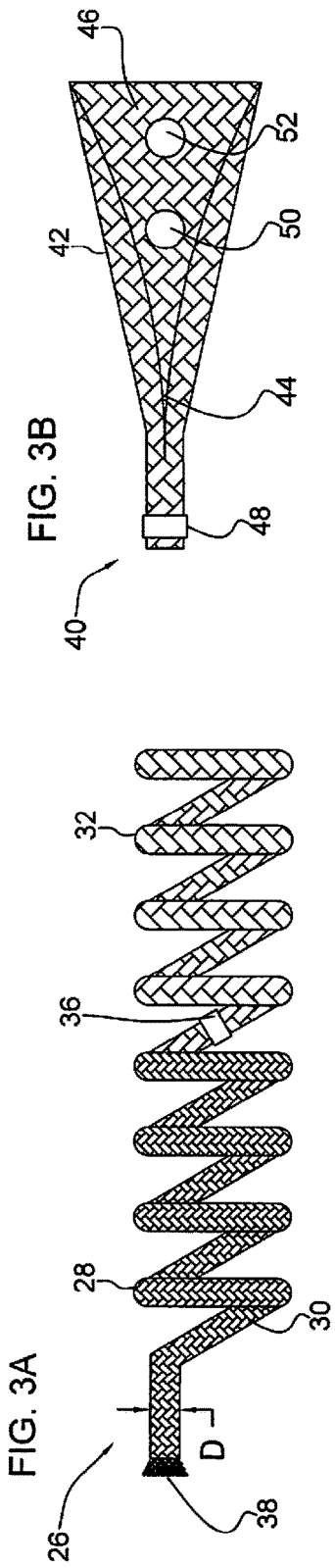

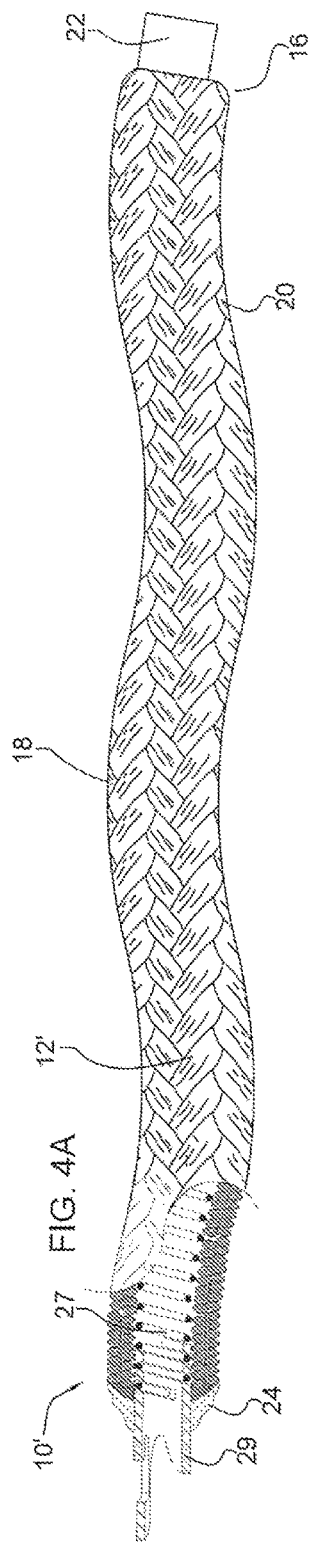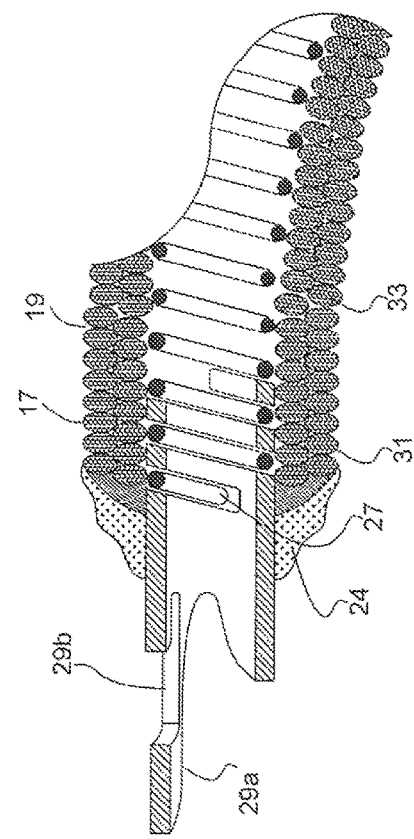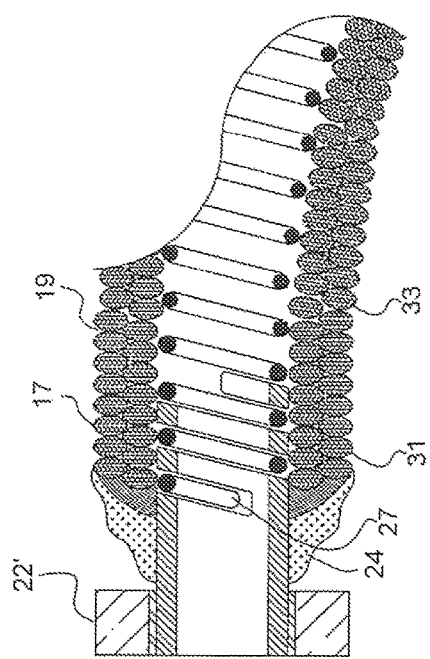
FIG. 4A
FIG. 4B
FIG. 4C

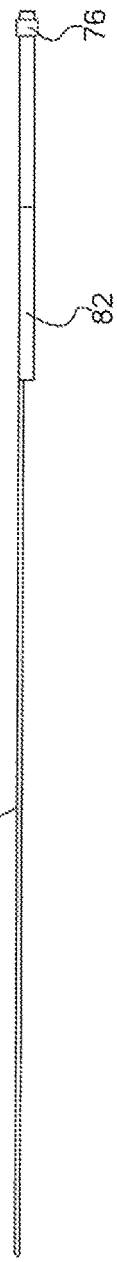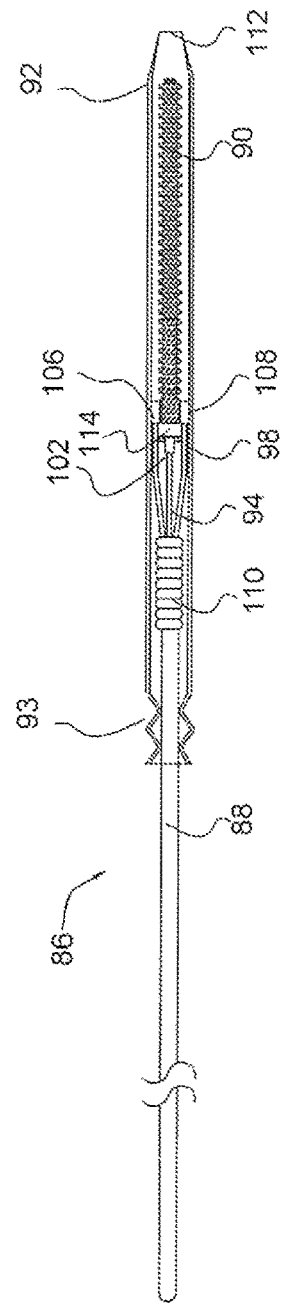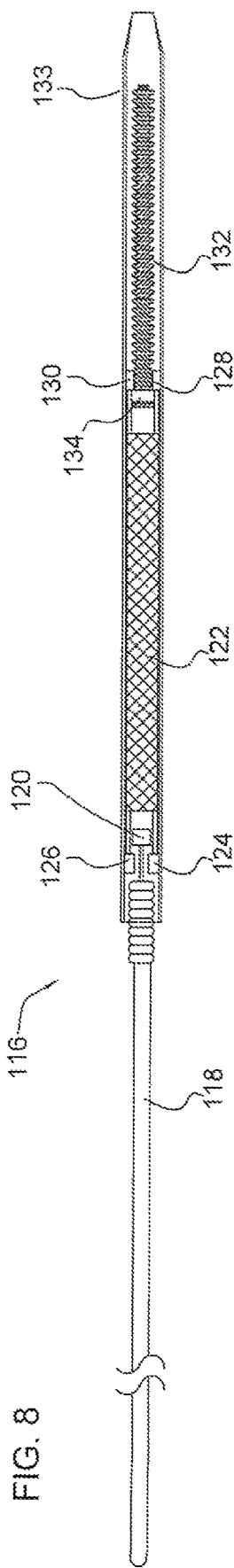
FIG. 6
FIG. 7
FIG. 8

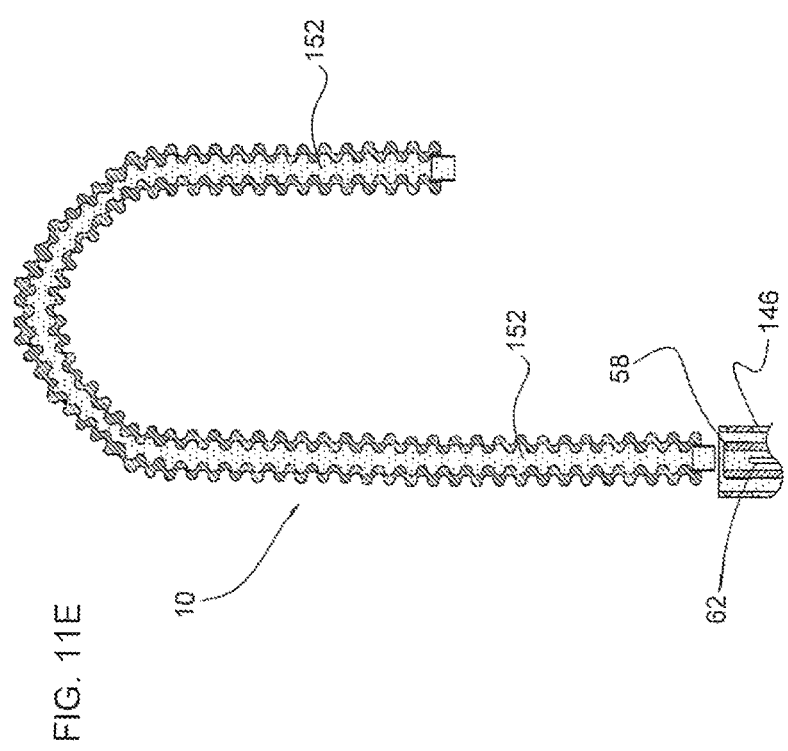
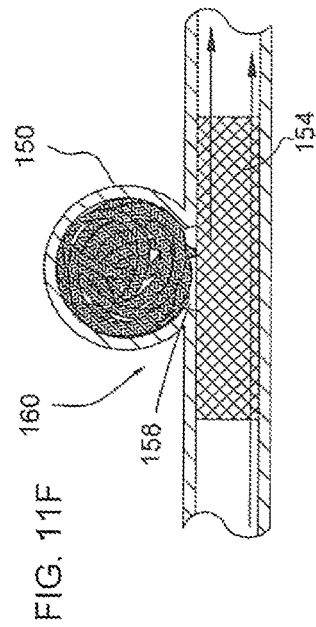
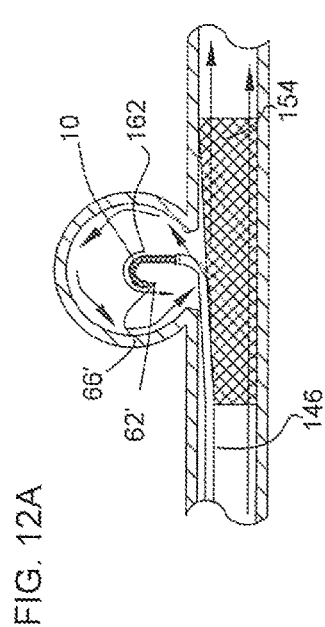
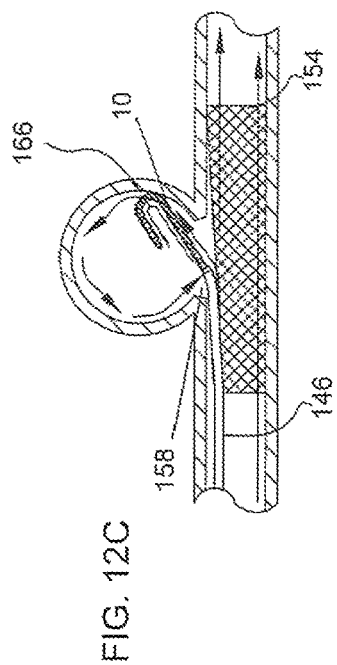

MICROGRAFT FOR THE TREATMENT OF INTRACRANIAL ANEURYSMS AND METHOD FOR USE

This application is a continuation of U.S. application Ser. No. 15/382,731, filed Dec. 18, 2016, which is a continuation of Ser. No. 14/997,008, filed Jan. 15, 2016, now U.S. Pat. No. 9,999,413, which claims priority from application 62/105,648, filed Jan. 20, 2015. The entire contents of each of these applications are incorporated herein by reference.

BACKGROUND

Technical Field

This application relates to medical devices, and more particularly, to vaso-occlusive devices used in the treatment of intracranial aneurysms.

Background of Related Art

An aneurysm is a localized, blood filled balloon-like bulge that can occur in the wall of any blood vessel, as well as within the heart. One endovascular treatment option for aneurysms is complete reconstruction of the damaged vessel using a vascular prosthesis or stent-graft. A stent-graft is an implantable tubular structure composed of two parts, a stent and a graft. The stent is a mesh-like structure made of metal or alloy which functions as a scaffold to support the graft. The graft is typically a synthetic fabric that is impervious to blood flow and lines the stent. Stent-grafts are not a treatment option for intracranial aneurysms due to the risk of cutting off blood flow to feeder vessels that may be vital for brain function. Stent-grafts can also be stiff, hard to deliver/retract, and can be highly thrombogenic within the parent vessel, all of which are undesirable features for intracranial aneurysm treatment. As a result, endovascular treatment of intracranial aneurysms has centered on packing or filling an aneurysm with material or devices in order to achieve a high packing density to eliminate circulation of blood, which leads to thrombus formation and aneurysm closure over time.

There have been a variety of materials and devices described for filling the sac of an intracranial aneurysm such as injectable fluids, microfibrillar collagen, polymeric foams and beads. Polymeric resins such as cyanoacrylate have also been used. Both are typically mixed with a radiopaque resin to aid in visualization. These materials pose a significant risk due to the difficulty of controlling dispersion and in retrieving them, if improperly or excessively delivered.

Mechanical vaso-occlusive devices are another option for filling an aneurysm. One type of mechanical vaso-occlusive device for the placement in the sac of the aneurysm is a balloon. Balloons are carried to the vessel site at the end of a catheter and inflated with a suitable fluid, such as a polymerizable resin, and released from the catheter. The main advantage of the balloon is its ability to effectively fill the aneurysm sac. However, a balloon is difficult to retrieve, cannot be visualized unless filled with contrast, has the possibility of rupture, and does not conform to varying aneurysm shapes.

Other types of mechanical vaso-occlusive devices are composed of metals or alloys, and biocompatible fibers, for example. Generally, the materials are formed into tubular structures such as helical coils. One of the earliest fibered coils was the Gianturco coil (Cook Medical). This coil was formed from a 5 cm length of 0.036" guidewire (inner core removed) and featured four 2 inch strands of wool attached to one tip of the coil to promote thrombosis. This device was difficult to introduce into tortuous vessel sites less than 3 mm in diameter. This is generally because the coil was stiff or bulky and had a high coefficient of friction.

Chee et al. (U.S. Pat. No. 5,226,911) introduced a more deliverable fibered coil with fibers that were directly attached to the length of the coil body. This coil was designed for more tortuous anatomy by decreasing the amount of thrombogenic material being delivered with the coil. Other examples of coils are U.S. Pat. No. 4,994,069 to Ritchart et al.; U.S. Pat. No. 5,354,295 and its parent, U.S. Pat. No. 5,122,136, both to Guglielmi et al.

Materials can also be formed into tubes/strings/braided sutures (see, e.g., U.S. Pat. No. 6,312,421 to Boock; U.S. patent application Ser. No. 11/229,044 to Sepetka et al.; U.S. patent application Ser. No. 13/887,777 to Rees; U.S. patent application Ser. Nos. 13/552,616 and 10/593,023 both to Wu et al.), cables (see, e.g., U.S. Pat. No. 6,306,153 to Kurz et al.), or braids. Metal coils can also be covered by winding on thrombogenic fiber as described in U.S. patent application Ser. No. 12/673,770 to Freudenthal and U.S. Pat. No. 6,280,457 to Wallace et al.

Unlike other tubular structures, braided or polymer coils can be further divided into non-expandable and self-expandable devices. These devices can be made from materials such as textiles, polymers, metal or composites using known weaving, knitting, and braiding techniques and equipment. Included in the weave or the finished braid can be optional mono or multifilament fiber manufactured to impart additional features or effects (e.g., radiopacity and thrombogenicity).

Non-expandable braids (see, e.g. U.S. Pat. No. 5,690,666 to Berenstein et al.; U.S. Pat. No. 5,423,849 to Engelson et al.; and U.S. Pat. No. 5,964,797 to Ho) can act as the implant and be mainly metallic, polymer, or a combination of metal and polymer. In such designs, braids have some minimal space between the filaments (braid strands) resulting in open cell designs. In addition, tight, mostly metal braids employing such designs result in stiff structures which are difficult to track via catheter or risk injury to the vasculature. Also, metal braided structures may be rough to the touch if not covered or further processed.

These braids can be formed into secondary shapes, such as coils that have little or no inherent secondary shape, they can be dimensioned to engage the walls of the aneurysm, or they can have other shapes (e.g. random, "flower", or three dimensional). These structures can also have a fiber bundle (s) in, or protruding from, the interior core made of natural fibers or thermoplastics infused with drugs to help with clotting (see, e.g., U.S. Pat. No. 5,423,849 to Engelson et al.; and U.S. Pat. No. 5,645,558 to Horton). Coiled braids can also be supplied with bio-active or other surface coatings (see, e.g., U.S. Pat. No. 6,299,627 to Eder et al.).

Non-expandable braids can also cover core or primary structures, such as coils or other braids (see, e.g., U.S. Pat. No. 5,382,259 to Phelps et al.; U.S. Pat. No. 5,690,666 to Berenstein et al.; U.S. Pat. No. 5,935,145 to Villar et al.; and U.S. Pat. No. 8,002,789 to Ramzipoor et al.). Much like the above braid structures, these covers have open cell designs (e.g., inner coil structure is visible through the braid).

Regardless of configuration, it is difficult to achieve high packing densities and rapid flow stagnation with these devices as they have open cell construction which allows at least some blood flow through the wall, may not compress adequately, and/or may have limited bend radii. If an aneurysm sac is not sufficiently packed to stop or slow blood flow, any flow through the neck of the aneurysm may prevent stasis or cause coil compaction, leading to recanalization of the aneurysm. Conversely, tight packing of metal coils in large or giant aneurysms may cause increased mass effect (compression of nearby tissue and stretching of aneurysm sac) on adjacent brain parenchyma and cranial nerves. Coil prolapse or migration into parent vessels is another possible issue with non-expanding devices, especially in wide neck aneurysms.

Braids may also be self-expanding and can be shaped into various forms such as a ball, a coil(s), and a combination braid-stent. Examples of self-expanding devices are disclosed in the following: U.S. Pat. No. 8,142,456 to Rosqueta et al.; U.S. Pat. No. 8,361,138 to Adams; U.S. patent application Ser. No. 13/727,029 to Aboytes et al.; U.S. patent application Ser. No. 14/289,567 to Wallace et al.; U.S. patent application Ser. No. 13/771,632 to Marchand et al.; and U.S. patent application Ser. No. 11/148,601 to Greenhalgh.

Self-expanding braids are expected to occupy all or substantially all of the volume of an aneurysm to obstruct flow and/or promote endothelization at the neck. A major problem for these designs is sizing. The implant has to be accurately sized so that upon expansion it occupies enough volume to fill the entire aneurysm, dome to neck. Undersized devices lead to insufficient packing as described above, whereas oversizing risks rupturing the aneurysm or blockage of parent vessel.

Neck bridges are yet another approach to treating intracranial aneurysms. They can be broken down into two categories: those that act as support to keep the coil mass from migrating into a parent vessel (coil retainer) and those that span the neck to obstruct flow into the aneurysm. Neck bridges that support the coil mass tend to be petal/flower shaped and span the neck of the aneurysm or placed between the parent vessel and aneurysm sac. Examples of neck bridges for supporting the coil mass are disclosed in the following: U.S. Pat. No. 6,193,708 to Ken et al.; U.S. Pat. No. 5,935,148 to Villar et al.; U.S. Pat. No. 7,410,482 to Murphy et al.; U.S. Pat. No. 6,063,070 to Eder; U.S. patent application Ser. No. 10/990,163 to Teoh; and U.S. Pat. No. 6,802,851 to Jones et al.

Neck bridges that obstruct flow through the aneurysm neck can be deployed either internal or external to the aneurysm and may not require deployment of embolization coils. Examples of intra-aneurysmal neck bridges with deployment at the base of the aneurysm sac with components extending into the neck are disclosed in U.S. Pat. No. 6,454,780 to Wallace; U.S. Pat. No. 7,083,632 to Avellanet et al.; U.S. Pat. No. 8,292,914 to Morsi; and U.S. Pat. No. 8,545,530 to Eskridge et al. Examples of neck bridges deployed external to the aneurysm (in the parent vessel) are disclosed in U.S. Pat. No. 6,309,367 to Boock; U.S. Pat. No. 7,241,301 to Thramann et al.; and U.S. Pat. No. 7,232,461 to Ramer; U.S. Pat. No. 7,572,288 to Cox; U.S. patent application Ser. No. 11/366,082 to Hines; U.S. patent application Ser. No. 14/044,349 to Cox et al.; U.S. Pat. No. 8,715,312 to Burke; U.S. Pat. No. 8,425,548 to Connor; and U.S. Pat. No. 8,470,013 to Duggal et al. Neck bridges can also have surface treatment to encourage neointima formation as disclosed in U.S. Pat. No. 6,626,928 to Raymond et al. Regardless of design, neck bridges pose several problems when treating intracranial aneurysms. The first major challenge is deployment of these devices, which requires the bridge to be maneuvered and often re-positioned over the aneurysm neck to assure complete coverage. Secondly, if recanalization occurs, any subsequent retreatment of the aneurysm will be hampered due to access being restricted by the neck bridge or one of its components.

Stents and flow diverters are similar to neck bridges in function, but are intended for parent vessel reconstruction and therefore run distal to proximal of the aneurysm, covering the neck. Such devices are deployed in the parent vessel and are intended to act as a physical blood flow barrier to induce sac embolization, stabilize embolic coils, and prevent coil protrusion and/or migration. Flow diverters, due to their relative low porosity (high coverage), can be used with or without coils and have been found to promote thrombus formation by restricting blood flow into the aneurysm sac. However, complications such as recanalization, delayed stent thrombosis, delayed aneurysm rupture, and stent migration have also been observed. An example of a stent is disclosed in U.S. Pat. No. 6,746,475 to Rivelli and a flow diverter is disclosed in U.S. Pat. No. 8,398,701 to Berez et al.

While the above methods attempt to treat intracranial aneurysms with minimally invasive techniques, there remains a need for a highly compliant and thrombogenic filler that blocks blood flow within the sac of the aneurysm without the drawbacks of current devices. For example, it would be advantageous to provide a device that achieves sufficient flexibility to enable advancement through the tortuous vasculature into the cerebral vasculature and achieves high packing densities while maintaining a high concentration of thrombogenic material. It would also be advantageous to provide such device which is simple in structure and simple to manufacture without sacrificing efficacy. Still further, since the device is designed for minimally invasive insertion, such device needs to be easy to deliver and deploy at the intracranial site as well as manufacturable in a small enough size for use in cerebral vasculature. All of this needs to be achieved with a construction that effectively packs the aneurysm without damaging the sac or other tissue while promoting rapid clotting and healing of an intracranial aneurysm with reduction in mass effect. To date, no device effectively achieves all these objectives, with current devices at best achieving one objective at the expense of the other.

SUMMARY OF INVENTION

The present invention provides an intra-aneurysmal micrograft that overcomes the above discussed limitations and deficiencies in treating aneurysms, especially intracranial aneurysms. The present invention also provides intra-aneurysmal micrograft delivery systems for delivering micrografts to an intracranial aneurysm.

In accordance with one aspect, the present invention provides a vascular graft configured for occluding a vasculature of a patient comprising:
  an absorbent biocompatible structure; and
  a core element having a proximal end, a distal end and a lumen within the core element, the core element positioned inside the biocompatible structure and attached to the biocompatible structure;
  wherein a capillary effect is created within the vascular graft when the biocompatible structure is exposed to blood such that blood is transported in a proximal direction through the vascular graft wherein blood clots.

In some embodiments, a lumen in the core element is dimensioned to transport blood in a proximal direction.

In some embodiments, the vascular graft is non-self-expanding. In some embodiments, the core element has a coiled structure and the graft further comprises a tube positioned within coils of the coiled structure. In some embodiments the vascular graft has an outer diameter less than 0.027 inches.

In some embodiments, the biocompatible structure is a textile structure which includes a plurality of yarns spaced to wick blood when placed in contact with blood. The plurality of yarns can each be formed by a plurality of fibers, the fibers spaced to wick blood when placed in contact with blood.

In some embodiments, the polymeric structure is crimped to form a series of peaks and valleys along a surface of a wall to increase flexibility The vascular graft can include a radiopaque element within the vascular graft. The vascular graft in some embodiments is shape set to a non-linear configuration wherein it is movable to a substantially linear configuration for delivery and returns to the same or different non-linear configuration for placement within the vasculature.

In some embodiments, the core element is made of a radiopaque material. In some embodiments, the core element is wound into an open pitch helical coil.

In accordance with another aspect of the present invention, an occluding device for treating an intracranial aneurysm of a patient is provided comprising an elongate tubular structure having a plurality of yarns and a longitudinal axis extending in a distal to proximal direction. The tubular structure is crimped to alter the shape of the yarns and provide a first series of peaks defined by the yarns and a first series of valleys formed between the yarns and a second series of peaks and second series of valleys formed in the tubular structure in a longitudinal direction to increase the flexibility of the tubular structure.

In some embodiments, each of the plurality of yarns is formed by a plurality of polymer filaments, the plurality of filaments having a first set of pores (capillary spaces) therebetween for absorption of blood to create a first capillary effect and the plurality of yarns having a second set of pores (capillary spaces) therebetween for absorption of blood to create a second capillary effect. In some embodiments, the plurality of yarns and plurality of filaments wick blood and the occluding device further has a lumen therein through which blood can flow into to create a third capillary effect. The lumen can include a distal opening for blood. In some embodiments, the occluding device is shape set to a non-linear configuration.

In accordance with another aspect of the present invention, a system for occluding a vasculature of a patient is provided comprising a vascular micrograft having an absorbent polymeric structure, a lumen for passage of blood therein, an outer wall, and a retaining structure attached to the vascular micrograft. A delivery element has an engagement structure cooperating with the retaining structure to retain the vascular micrograft during insertion by the delivery element through the vasculature.

In some embodiments, the micrograft is positioned coaxially on the delivery element.

In some embodiments, the retaining structure includes a radiopaque marker band positioned within an internal portion of the vascular micrograft and the engagement structure includes a taper on the delivery element for frictionally engaging a proximal portion of the vascular micrograft. In other embodiments, the engagement structure includes a plurality of members movable from a first expanded position to a second grasping position to grasp the retaining structure.

In some embodiments, the retaining structure includes a tab movable between a first engaged position and a second non-engaged position.

The system can further include a pusher catheter (member), the delivery element extending through the pusher catheter, and the micrograft having a diameter less than 0.027" for delivery through a microcatheter to an intracranial aneurysm.

In accordance with another aspect of the present invention, a system for treating an aneurysm in a vessel of a patient is provided comprising:
 an implantable occluding device configured for introduction into a lumen of the vessel, the occluding device having a first lumen for passage of blood therein;
 a delivery member, the occluding device mounted on the delivery member such that a portion of the delivery member extends into the first lumen of the occluding device; and
 a catheter having a second lumen, the delivery member extending through the second lumen;
 wherein proximal movement of the delivery member exposes the first lumen for passage of blood therethrough in a capillary action as blood displaces the delivery member as the delivery member is withdrawn proximally from the first lumen.

In some embodiments, the delivery member extends distally beyond the occluding device during delivery of the occluding device to the aneurysm. In some embodiments, the occluding device has a porous outer wall.

In some embodiments, a clearance between an outer dimension of the delivery member and an inner dimension of the occluding device is substantially fluid-tight before delivery into the aneurysm but sufficient to enable slidable movement of the delivery member with respect to the occluding device.

In some embodiments, the delivery member is configured for delivery through a catheter having a diameter less than or equal to 0.027".

In some embodiments, the catheter has a distal portion in abutment with the occluding device to advance the occluding device off the delivery member into the aneurysm.

In some embodiments, the occluding device is a polymer structure formed as a non-expanding braid composed of multiple multi-filament yarns of polymeric material. In some embodiments, the polymer structure is absorbent and wicks blood via a capillary action in a distal to proximal direction.

In some embodiments, the occluding device includes retaining structure engageable with an engagement structure of the delivery member to retain the occluding device on the delivery member.

In some embodiments, the occluding device is shape set to a non-linear configuration and advanceable from a substantially linear configuration coaxially positioned on the delivery member to the same or different non-linear configuration placed within the aneurysm.

In accordance with another aspect of the present invention, a method for treating an intracranial aneurysm is provided comprising the steps of:
 a) providing an occluding device having a lumen therein;
 b) providing a delivery member;
 c) inserting the delivery member with the occluding device into the aneurysm, the delivery member retaining the occluding device during delivery of the occluding device to the aneurysm;
 d) retracting the delivery member proximally within the lumen of the occluding device to provide a gap for blood flow in the lumen of the occluding device; and e) subsequently moving a pusher member to advance the occluding device off the delivery member.

Preferably, the delivery member is inserted into a microcatheter for delivery to the aneurysm.

In some embodiments, the occluding device is assembled of fibers forming a fibrous structure.

In some embodiments, the delivery member is inserted into the pusher member prior to advancing the delivery member through a microcatheter to the aneurysm.

In some embodiments, the step of retracting the delivery member includes retracting the delivery member until it is aligned with a marker band attached to the occluding device.

In some embodiments, the occluding device is preset to a non-linear configuration and advancement of the occluding device into the aneurysm returns the occluding device from a substantially linear configuration coaxially positioned on the delivery member for delivery to the same or different non-linear configuration placed within the aneurysm.

In some embodiments, the delivery member is a wire having a curved or shaped tip.

In some embodiments, the step of inserting the delivery member includes the step of passing the delivery member through a catheter positioned in a stent in the vasculature. In some embodiments, the occluding device can be guided within the aneurysm by the delivery member.

In accordance with another aspect of the present disclosure, a method for manufacturing a vaso-occlusive device is provided comprising the steps of:
  a) braiding a series of multifilament yarns over a mandrel to create a braid having an elongate body of coaxially aligned filaments having a proximal portion, a distal portion, and a lumen extending therebetween along a longitudinal axis;
  b) compressing the elongated body longitudinally over the mandrel until the elongate body buckles creating a sinusoidal shape having a series of peaks and valleys along a length of the body and bundles of individual filaments of the multifilaments within the yarns orient substantially transversely to a longitudinal axis of the mandrel to create a series of smaller peaks and valleys along the length of the body;
  c) after step (b) heat setting the braid to set the peaks and valleys; and
  d) removing the braid from the oven.

In some embodiments, an internal stop extends from the body of the device for cooperation with a delivery member. In some embodiments, the step of braiding leaves pores between the series of multifilament yarns.

The present invention also provides in some aspects methods for filling and infusing an intra-aneurysmal micrograft with blood or another liquid and delivering it to an intracranial aneurysm.

The present invention also provides in some aspects a system for viscosity based retraction of intra-aneurysmal micrografts back inside a catheter.

In one aspect, an intra-aneurysmal micrograft is provided having a tubular body that has a textile construction with a through lumen that has a series of peaks and valleys, or a wavy profile (dependent on wall thickness), running longitudinally across its length. At either end of the tubular body, bands can be provided which may optionally be radiopaque and/or used for mating to a delivery system. In another form of the construction, one or both ends of the graft can be shape set with a "J" or curl or other shape that help with delivery. In yet another form of the construction, agents can be added to the inner or outer diameter of the tubular body to aid in delivery (visualization), cancer treatment and/or endothelial cell growth.

In some embodiments, the micrograft has a variable stiffness tubular structure that has been shape set to have secondary shapes such as a helical coil. The change in stiffness may be indicated by a radiopaque marker band or reduced/compressed section. In some embodiments, a single end or both ends of the micrograft can be frayed to create Velcro-like locks that mate with other micrografts sharing the same feature.

In some embodiments, the micrograft structure is formed to be directable by blood flow. The micrograft may be cut longitudinally and shape set to expose an inner surface or it may be a tubular form. Additionally, the micrograft may have holes or slots.

In any of the foregoing, the micrograft can be formed using a braided multi-filament polyester (e.g., PET) yarn, but it may be formed of other flexible mono or multi-filament fibers, yarns, or textile materials.

In one embodiment of a delivery system, a delivery wire with one or more pre-mounted micrografts is inserted into an over-the-wire pusher catheter having a through lumen. In some embodiments, the delivery wire is a guidewire pre-mounted with one or more micrografts. In yet another embodiment, the micrograft is loaded on the primary guidewire used during a procedure. In some embodiments, the pusher catheter is a rapid exchange catheter.

In one embodiment of the delivery system, a pusher wire with grasper arms with bands engages a band, or thickened section, on a proximal end of the micrograft inside a delivery tube.

In another embodiment of the delivery system, a push wire engages a stent or flow diverter device which in turn engages a micrograft inside a delivery tube.

In another alternate embodiment of a delivery system, a micrograft is loaded into an introducer tube and used in combination with a pusher catheter (member).

In accordance with one aspect of the present invention, a method of placing and deploying a micrograft is as follows. A pre-loaded delivery wire with a micrograft is loaded into a pusher catheter (proximal end of wire loaded into distal end of pusher catheter) until the distal end of the pusher contacts the micrograft. This system is then advanced to an aneurysm through a microcatheter that has been previously placed at the intended anatomical site. Once the delivery wire and distal end of the micrograft reach the tip of the microcatheter, the delivery wire tip is pulled back inside the micrograft just distal of the lock. As the wire is drawn back, blood fills the volume displaced by the wire inside the micrograft. Once filled with blood, the delivery system is advanced until the micrograft is deployed. When placed in the desired position, the micrograft is detached by retracting delivery wire tip, or further advancing pusher catheter, until the tip of the wire pulls through the lock and into the pusher. In this method, as long as the wire tip remains distal to the micrograft lock, the micrograft can be retrieved. Once the micrograft is deployed, the delivery system is removed and, if necessary, another pre-loaded delivery wire is selected and the process for delivering a micrograft is repeated until the aneurysm is sufficiently packed with micrografts.

In an alternate method, multiple micrografts are loaded onto a single delivery wire. In some embodiments, instead of the delivery wire, a standard guidewire is loaded with a micrograft of the present invention during the procedure and the guidewire with loaded micrograft can be used as a primary access wire. The pusher catheter in an alternate embodiment is a rapid exchange catheter.

In some embodiments of the delivery method, the micrograft is directed for placement within the aneurysm using either a shaped delivery wire or the microcatheter tip.

In some embodiments a micrograft is directed by blood flow once released from the microcatheter.

In some embodiments of the delivery method, the proximal end of the micrograft is locked by a series of arms extending distally from a push wire that are compressed by advancing a loading tube. In such method, to deliver the micrograft, the distal end of the loading tube is inserted into a microcatheter luer and locked in place with the Rotating Hemostatic Valve (RHV). The push wire with micrograft is then advanced through the microcatheter until it reaches the distal tip of the catheter. The micrograft is deployed by pushing the arms of pusher wire out of the microcatheter so they can expand and release the micrograft. The pusher arms can then be used to move the micrograft around in the aneurysm or to grasp and retrieve it. Like the previous method, this process can be repeated to insert additional micrografts until the aneurysm is densely packed.

In some embodiments of the delivery method, the micrograft is delivered in tandem with a stent or flow diverter through a microcatheter.

In some embodiments, a micrograft is pushed through a microcatheter into an aneurysm without a delivery wire.

These and other features of the invention will become more fully apparent when the following detailed description is read in conjunction with the accompanying drawings.

BRIEF DESCRIPTION OF THE DRAWINGS

FIG. 1 is a side view partial cut away of an intra-aneurysmal micrograft in accordance with one embodiment of the present invention;

FIG. 2A is a view of another embodiment of the intra-aneurysmal micrograft of the present invention having a larger diameter and thinner wall;

FIG. 2B is a side view similar to FIG. 2A except showing the micrograft stretched to highlight the peaks and valleys;

FIG. 2C is a side view of the micrograft of FIG. 2A in a bent placement position;

FIG. 3A is a side view of another embodiment of the intra-aneurysmal micrograft formed into a helical shape;

FIG. 3B is a side view of another embodiment of the intra-aneurysmal micrograft having a flared end to be directed by blood flow;

FIG. 4A is a side view partial cut away of an intra-aneurysmal micrograft in accordance with another embodiment of the present invention;

FIG. 4B is an enlarged view of one end of the micrograft of FIG. 4A;

FIG. 4C is side view of one end of an alternate embodiment of the micrograft of the present invention;

FIG. 6 is a side view of a rapid exchange pusher catheter for micrograft delivery in accordance with another embodiment of the present invention;

FIG. 7 is a side view of another embodiment of the intra-aneurysmal micrograft delivery system of the present invention having a pusher wire with locking arms;

FIG. 8 is a side view of another embodiment of the intra-aneurysmal micrograft delivery system of the present invention using a stent or flow diverter to push the micrograft;

FIGS. 11A-11F illustrate delivery of an intra-aneurysmal micrograft into an intracranial aneurysm in accordance with an embodiment of the present invention wherein:

FIG. 11A shows the delivery wire inserted into the aneurysm sac;

FIG. 11B shows initial advancement of the micrograft into the intracranial aneurysm after removal of the wire;

FIG. 11C is an enlarged cross-sectional view of the micrograft exiting from the catheter corresponding to the position of FIG. 11B;

FIG. 11D shows the micrograft fully deployed from the catheter and positioned in the intracranial aneurysm;

FIG. 11E is an enlarged cross-sectional view of the deployed blood-filled micrograft corresponding to the position of FIG. 11D;

FIG. 11F shows multiple micrografts of FIG. 11E positioned in the intracranial aneurysm sac;

FIGS. 12A-12C illustrates directed delivery by the delivery wire of an intra-aneurysmal micrograft into an aneurysm in accordance with an embodiment of the present invention;

DETAILED DESCRIPTION

Figure 4D:
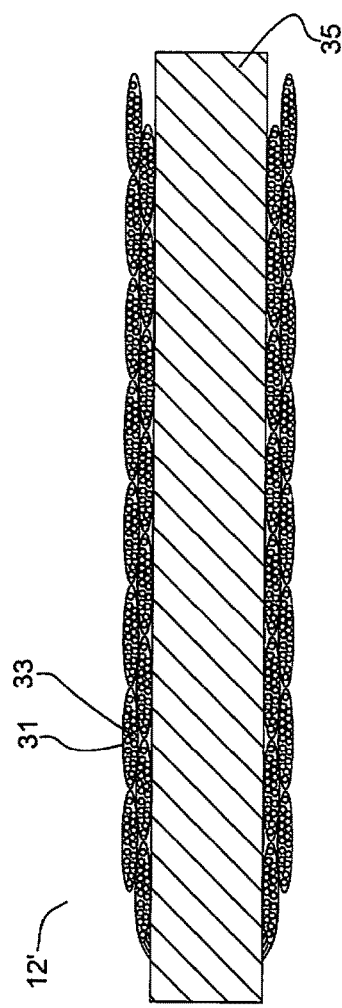
FIG. 4D is a cross-sectional side view of the micrograft of FIG. 4A placed over a mandrel before crimping.

The following embodiments are described in sufficient detail to enable those skilled in the art to practice the invention, and it is understood that structural changes may be made without departing from the scope of the present invention. Therefore, the following detailed description is not to be taken in a limiting sense. Where possible, the same reference numbers are used throughout the drawings to refer to the same or like components or features.

FIG. 1 illustrates a partial cut away side view of an intra-aneurysmal micrograft for insertion into an intracranial aneurysm in accordance with one embodiment of the present invention. The micrograft of this embodiment, designated generally by reference number 10, includes a biocompatible non-self-expandable absorbent braided polymeric textile tubular body 12 that has been crimped to reduce stiffness and increase wall thickness and fabric density. The micrograft 10 has sufficient stiffness as well as sufficient flexibility to provide the advantages described below. It further is structured to enable a triple capillary action to promote blood clotting as also discussed in detail below. The micrograft further preferably has a high surface area for increased blood absorption, is radially deformable, has a low friction surface for ease of delivery and can be shape set to enhance packing of the aneurysm. These features and their advantages are described in more detail below. Note the micrografts of the present invention are especially designed to induce blood stagnation or clot to rapidly treat the aneurysm. The micrografts are configured for delivery to an intracranial aneurysm, although they can be utilized for occlusion in other aneurysms in other areas of the body as well as for occlusion in other vascular regions or in non-vascular regions.

An over the wire delivery system is provided to deliver the micrograft of the present invention to the aneurysm. Variations of these delivery systems of the present invention are discussed in detail below. Preferably, multiple micrografts are delivered so that the aneurysm sac is densely packed.

Turning first to the biocompatible micrografts of the present invention (the delivery systems are subsequently discussed) the preferred tubular body 12 of micrograft 10 is constructed of substantially 100% 20 denier/18 filament polyester (e.g., PET) multi-filament interlaced yarns, but can be made of other combinations of denier and filament such as 10 denier/16 filament yarn, or 15 denier/16 filament yarn, for example. That is, each yarn is composed of a plurality of polyester filaments having pores or spaces therebetween, and the plurality of yarns also have pores or spaces therebetween, for reasons described below. The tubular body has a proximal end 14 and a distal end 16, with proximal defined as closer to the user and distal defined as further from the user such that the distal end is inserted first into the aneurysm. Blood then flows through the micrograft 10 in a distal to proximal direction. The tubular body 12 has a preferred inner diameter in the range of about 0.001 inches to about 0.068 inches, and more narrowly in the range of about 0.006 inches and about 0.040 inches, for example about 0.008 inches. It has a length ranging from about 2 mm up to about 150 cm and a preferred outer diameter in the range of about 0.002 inches to about 0.069 inches, more narrowly in the range of about 0.010 inches to about 0.041 inches, for example about 0.010 to about 0.020 inches. Note that although these ranges and dimensions are the preferred ranges and dimensions, other ranges and dimensions are also contemplated. These dimensions provide a sufficiently small size micrograft so that the micrograft can be navigated to and into the cranial vasculature for placement within a cranial vessel.

Each of the multi-filament yarns are made of multiple wettable micro-filaments, or fibers, assembled with spaces (pores) between them, referred to as inter-fiber spaces or pores. The pores are sufficiently sized to induce capillary action when contacted by a liquid, resulting in the spontaneous flow of the liquid along the porous yarn (i.e., wicking). This capillarity between fibers (intra-fiber) within the yarn is termed as "micro-capillary" action. As a result, a sufficiently wettable and porous yarn will have high wickability and transport liquid along its length. The multiple filaments also provide a high surface area and can be hydrophilic or hydrophobic.

This assembly of the two or more wickable multi-filament yarns into a permeable structure (such as a textile) results in a "macro-capillary" action, i.e., the transporting of liquid between the yarns and throughout the structure. Such yarns and/or fibers can be textured, flat, twisted, wettable, non-wettable, with beads, of various cross-sections (tri-lobal, multi-lobal, hollow-round, etc.), coated or having a modified surface, composite, reticulated, porous, pre-shrunk, crimped or modified using similar heat treatment or chemical processes.

The multi-filament yarns can be assembled into a textile tubular structure using a braider or other textile manufacturing equipment and methods. In general, the braider can be set-up with a program or recipe, spools of multi-filament yarn and an optional core mandrel to braid over. Anywhere from about 8 to about 288 strands of multi-filament yarn may be used to form the tube, depending on the desired final structural properties such as density, picks per inch (PPI), porosity, compliance, etc. If desired, multiple braiders or a braider in combination with a coil winder can be run simultaneously to form a braid over braid or braid over coil design.

The micrograft 10 is braided over the core mandrel which sets the internal diameter (ID) of the braid. The core mandrel can be made of a variety of materials such as metal, wire, polymers or other textile fibers. It can also be formed of a stretchable material to aid in removal during manufacturing.

The micrograft 10 can also include a permanent core element such as shown in the embodiment of FIG. 4A discussed below. The core element can be made of a variety of materials, and can itself be formed of one or more filaments, and may optionally be coated. In one embodiment, the core element is formed of a metal coil having a lumen therein. It can be composed of platinum-iridium or other materials. The braid and coil can be heat set at a temperature that would not damage or disintegrate the braid.

The braiding process may be adjusted for the highest PPI possible so as to produce a tightly interlaced, dense braid without tenting (braiding over itself or overlapping). However, in some cases tenting may be desirable to produce a useable feature such as a braid bulge or ring for locking or wall thickening. The braid, while still mounted on the core mandrel, may be heat treated after manufacturing to set the braid structure, including PPI, and to relieve filament stresses produced during braiding.

The preferred PPI for the as-braided therapeutic structure, for example, may range from about 80 to about 200 PPI for a 16 strand braid, and more narrowly in the range of about 120 to about 180 PPI, preferably about 167 PPI. The PPI is dependent on the number of strands used to braid, the braid angle, and the braid diameter, such that a braided tube of a given diameter with 120 PPI and 16 strands would have a PPI of 60 when braided using 8 strands at the same diameter (assuming all of the variables constant). The preferred PPI should be high enough to produce a dense interlacing pattern, but not so high as to interfere with core mandrel removal, unless the core is stretchable. Crimping, which will be discussed later in detail, may be used to increase PPI (and braid angle), once again depending on final structural requirements.

The use of multi-filament yarns in combination with a relatively high PPI of the present invention results in a somewhat stiff, relatively small or closed cell (high pick density) braided tube. As mentioned above, there is a micro-capillary effect resulting in wicking of liquid along the porous yarns due to inter-fiber spaces and a macro-capillary effect resulting in liquid flow between yarns and throughout the textile wall due to inter-yarn porosity associated with using a wettable multi-filament yarn. Due to the manufactured tube's relatively small inner diameter and a sufficiently dense interlacing braid pattern (i.e., a filamentary wall structure with sufficiently small pore size such that it retains fluid), a third capillary effect is created. When properly sized, this third capillary effect is responsible for spontaneous flow of liquid inside the micrograft lumen, e.g., within the lumen of the braid, in a proximal direction. The liquid can also spread in other directions as it is absorbed. This structure thus results in a soft capillary tube that has absorbent walls. This triple capillary effect is beneficial for a vaso-occlusive device due to the fact that the yarns, the fibrous wall, and the micrograft lumen can become saturated with blood. Since blood absorbed by the micrograft is trapped within the structure, it becomes stagnant and will quickly thrombose or form clot.

To achieve the capillary and clotting characteristics, the micrograft 10 achieves an optimal balance of porosity and fluid containment within the same structure. This is achieved by controlled interlacing of microporous yarns that allow blood wicking and cell ingrowth. When braided with sufficiently high PPI and tension, for example, the porous yarns are able to form a fluid barrier that maintains a degree of permeability. The resultant structure (textile tube) is an assembly of micro-porous yarns that may be interlaced with sufficient density to form a fluid-tight tubular capillary. This interlacing of the yarns or assembly of filaments can be achieved using textile manufacturing processes, such as weaving, knitting, or electrospinning. Porous or semi-porous filaments may also be used in place of multi-filament yarns to achieve desired absorbency. Additionally, the micrograft structure does not have to include a clearly defined inside lumen to maintain capillarity, e.g., a defined lumen formed within the wall of the braid or core element, but may alternatively be a porous assembly of fibers sufficiently spaced to allow transport of liquid (much like a suture or string wicking liquid) or a porous scaffold or biocompatible open cell foam.

While the semi-porous micrograft 10 as formed as described above has the desired effect of aiding thrombus formation, it is also relatively stiff as a result of the filaments being closely packed or tightly braided as mentioned above. One benefit of a stiff, denser braid is its ability to retain its non-linear heat-set shape as compared with lower PPI (less dense) braids. This may facilitate the use of stiffer, higher density 3D shaped micrografts as framing-type devices used for initial filling of aneurysm circumference, and then soft and highly compliant micrografts may be used as fillers or "finishing" devices towards the end of the embolization procedure. For example, a dense (or high PPI) 2×2 (two-over-two) configuration braid may be used as the initial "framing" device whereas a softer and more compliant braid having a lower-PPI 1×2 (1-over-2-under-2) configuration braid may be subsequently used to fill the framed space within the first device. However, even if used as a framing device, excessive stiffness is an undesirable mechanical property for the microcatheter delivery because an overly stiff device may cause unwanted movement of the microcatheter tip during delivery which can adversely affect navigation of the microcatheter or damage vessels during advancement through the tortuous vasculature. Excessive stiffness is also an undesirable property because stiff devices will conform less to the configuration of the aneurysmal sac and thus prevent efficient aneurysm packing.

Therefore, to reduce stiffness to assist delivery and packing of the aneurysmal sac, the micrograft tubular body (braid) 12 is crimped during manufacture, i.e., longitudinally compressed and heat set. As the braid 12 is compressed, axial orientation of the braided strands is reduced thereby increasing braid angle with respect to the longitudinal axis of the tubular body which reduces their influence on overall stiffness of the structure, much like a straight wire taking on a more flexible form when coiled. Crimping will also effectively increase the PPI, wall thickness, and linear density of the braid by axially compressing the structure and filament bundles. This compression causes an outward radial expansion and an increase in wall thickness of the tube. The resulting braid is much more deflectable, has reduced bend radius, a higher density and up to 2× to 3× or higher increase in PPI, depending on braid structure and compressive force applied.

This axial compression also causes the braid structure to "snake" or produce a spiral wavy form as shown in FIG. 1, which as viewed from the side is a series of macro peaks and valleys, termed "macro-crimps" in a sinusoidal shape. The sinusoidal undulations (macro-crimps) are typically more pronounced in braid structures where the ratio of wall thickness to overall braid diameter is larger (i.e., overall diameter decreases). Sufficient crimping may also re-orient individual yarn fiber bundles from a mostly flattened (longitudinally organized cross-section) state to a compressed (transversely organized cross-section) state. This increases surface unevenness of the braid since individual yarns bulge outward and produce micro peaks and valleys on the braid surface, termed "micro-crimps" (see FIG. 4B for example) with the peaks 17 located at the height of the yarn and the valleys 19 between adjacent yarns.

The braid can have a series of coaxial aligned filaments and compressed so the filaments orient substantially transversely (with respect to a longitudinal axis of the mandrel).

Different braid patterns (such as 1×1, 1×2, or 2×2, etc.) may also produce varied results when crimped. For example, a 1×1 braid structure will tend to have a more uniform tubular shape and less distinctive macro-crimp pattern, whereas a 1×2 braid structure will produce a more sinusoidal (macro peaks and valleys) crimped structure in addition to the micro peaks and valleys (micro-crimps) of individual fiber bundles. These structural changes result in an ultradeflectable, increased density, wavy-wall structure having macro-peaks 18 and valleys 20 as shown in the sinusoidal shape of FIG. 1A.

Besides increasing braid flexibility, PPI and/or wall thickness, varying amounts of crimping imparts other potentially desirable features such as kink and crush resistance, reduced bend radius, as well as increased surface area per unit length via accordion-like compression of the wall (i.e., forming peaks and valleys). The uneven texture of crimped peaks and valleys also helps create localized hemodynamic turbulence and flow stagnation, resulting in improved thrombus formation. The crimps make the device more compliant, easily deflectable and conformable which facilitates packing confined spaces or voids in the vasculature, e.g., the aneurysm. Crimping may also be used to vary wicking and permeability of the textile wall since it reduces fabric porosity and increases yarn tortuosity.

The location, amount and magnitude of crimping can be controlled to impart different amounts of flexibility and elongation to the structure to achieve its desired characteristics. For example, extreme crimping can be applied so the braid is compressed until the individual fibers within each yarn bundle come together and cannot compress any further, giving the braid some rigidity and improving pushability through a microcatheter lumen. Other factors that impact crimping and the resulting longitudinal pattern are fiber diameter and stiffness, yarn tension during braiding, wall thickness, wall porosity (PPI), number of filaments, and mandrel diameter.

Figure 16A:
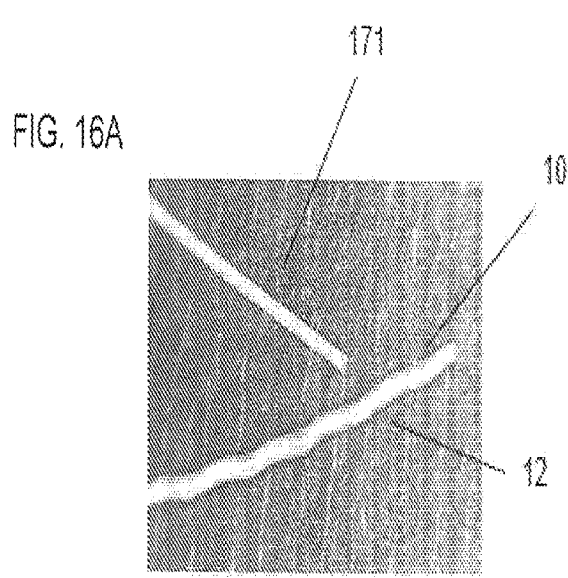
FIG. 16A is a photograph of an uncrimped tubular PET braid alongside a crimped braid of the present invention to show a wave-like profile as in FIG. 1A.

For example, larger diameter, thin walled tubular bodies (braids), i.e., low wall thickness to outer diameter ratio, may show macro peaks and valleys which are more dense and visible than small, thick walled crimped tubes. FIGS. 2A-2C show an example of such large diameter thin walled tube where crimping can form an accordion-like folds or pleat structure rather than a sinusoidal configuration as the peaks are closer together. Crimping smaller diameter braids (braids with higher wall thickness to outer diameter ratios) typically induces a wave-like, sinusoidal longitudinal (macro) contour that is larger in comparison to overall diameter and increases wall thickness of the structure, as shown in FIG. 16A. It should be noted the sinusoidal contour is typically three-dimensional in form (like a spiral) and is visible from all sides of the braid. During crimping, the ends of the tubular body may also be rotated/twisted relative to each other and then heat set as another method to impart deflectability to the tubular body.

The braid 10 can also be made more flexible by varying the braid angle or PPI, by reducing yarn tension, by adding cuts/slits, changing the number of filaments or strands, or heat setting repeating patterns along its length (such as flat sections or kinks). If a stiffer tube is desired, denser yarn and/or braid pattern may be used or crimping decreased. Additionally, the micrograft structure may incorporate a coaxial construction (i.e., having a graft inside a graft) or multi-ply or multi-lumen wall design, especially when using fine-denier textiles. Intra-luminal braid inserts, such as the coils mentioned above, may also be composed of, or coated with, a highly wettable/hydrophilic material to enhance the capillary effect. For example, the micrograft may be coaxially assembled with a secondary braid or internal coil structure that is highly hydrophilic and/or radiopaque, while maintaining the therapeutic external surface.

The tubular body 12 may be braided, woven or knitted, partially or completely, from monofilaments or multi-filament yarns, strands, sutures, microfibers, or wire that is synthetic, semi-synthetic, natural or thermoplastic. Such materials may include, but are not limited to, Dacron, poly ester amide (PEA), polypropylene, olefin polymers, aromatic polymers, such as liquid crystal polymers, polyethylene, HDPE (high density polyethylene), ultra-high-molecular-weight polyethylene (UHMWPE, or UHMW), polytetrafluoroethylene (PTFE), ePTFE, polyethylene terephthalate (PET), polyether ketone (PEK), polyether ether ketone (PEEK), poly ether ketone ketone (PEKK), nylon, PEBAX, TECOFLEX, PVC, polyurethane, thermo plastic, FEP, silk, and silicone, bio-absorbable polymers such as polyglycolic acid (PGA), poly-L-gllycolic acid (PLGA), polylactic acid (PLA), poly-L-lactic acid (PLLA), polycaprolactone (PCL), polyethyl acrylate (PEA), polydioxanone (PDS) and pseudo-polamino tyrosine-based acids, extruded collagen. Metallic, metallic alloy or radiopaque material may also be included, Such material may be in the form of strands or filaments and may include, for example, platinum, platinum alloys (platinum-iridium or platinum-gold, for example), a single or multiple stainless steel alloy, nickel titanium alloys (e.g., Nitinol), barium sulfate, zinc oxide, titanium, stainless steel, tungsten, tantalum, gold, molybdenum alloys, cobalt-chromium, tungsten-rhenium alloys.

The use of different manufacturing methods or materials to construct the tubular body may have an impact on the capillary effects discussed earlier. For example, a change in material or construction methods may result in a simple capillary tube with capillary flow restricted to only the inner lumen of the tube, and not the walls. It should be understood by those skilled in the art that strands or filaments may be braided, interwoven, knitted, or otherwise combined to form a fabric or textile structure.

With reference now to the drawings showing exemplary embodiments of the micrograft of the present invention, the micrograft 10 of FIG. 1, as discussed above has a tubular body 12 with a proximal end 14 and a distal end 16.

Figure 17:
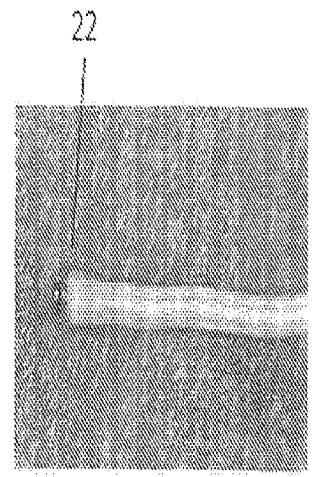
FIG. 17 is a photograph of one end portion of the micrograft of FIG. 1A.

To provide radiopacity so the device is visible under fluoroscopy (x-ray), the micrograft 10 can include radiopaque marker bands 22 which are inserted into the ends of the micrograft 10. FIG. 17 is a picture of an end of micrograft 10 with such marker band. The marker bands, which can also be in the form of coils, can be made from tantalum, platinum, platinum alloys (e.g., platinum-iridium alloy), gold, tungsten, or any suitable radiopaque material such as radiopaque polymer. The marker bands 22 are preferably approximately 1 mm or less in length and can be either of a sufficient inner diameter to slide over tubular body 12 or of a smaller diameter to fit inside the tubular body 12. FIG. 1 shows an example of the marker bands 22 fit inside the tubular body and the marker bands 22 can be secured by melting of the braid over the bands (the melted fiber) at region 24, or attached by gluing. The bands 22 can also be undersized and sliced lengthwise so that they can be swaged or folded over the outside of tubular body 12, or tubular body 12 can be stretched so that undersized bands can be slid over the stretched/compressed length in order to attach the bands 22 to the tubular body 12. In alternate embodiments, the bands can be flared at one end.

Although two marker bands are shown, in alternate embodiments, there may be one band or more than two bands placed around the tubular body along portions of its length to improve radiopacity. The bands positioned along the length can be in lieu of or in addition to a marker band at one end or a marker band at both ends. A radiopaque fiber can be utilized to connect the bands, and the radiopaque fiber incorporated into the textile structure, or placed inside the tube. The bands can be composed of metal, or alternatively of a non-metallic material such as radiopaque shrink tubing or polymer.

The marker bands can be adhered to the tubular body 12 using adhesive, mechanically by swaging or winding directly on to the tubular body, or by heating (when possible) and melting one of the materials. The bands can alternatively be attached by being screwed onto or into the core element, e.g., a helical core element, as discussed below.

As an alternative or in addition to the marker bands, radiopacity can be obtained by coating, wetting, staining, or impregnating the micrograft with a radiopaque material such as contrast media solution or nanoparticles. This can be done in manufacturing or in the operating room as part of the clinical procedure. The fibers or yarns themselves may be doped or impregnated or coated with radiopaque substances as described above. The micrograft may also contain a series of equally spaces radiodense inserts along its length, resulting in intermittent radiopacity which may be sufficient for visualization in clinical settings.

In addition to providing radiopacity, bands 22 can also be used to indicate structural changes in tubular body 12, as a means to control fraying, or as an integral part of the delivery system (e.g., stop-collar) as will be better understood in the discussion below of the delivery of the micrograft.

As another alternate to the bands, laser cut Nitinol structures that are made increasingly radiopaque can be utilized. These structures can be glued, melted over, sewn or otherwise attached to the proximal and/or distal ends of the micrograft, either on the inner or outer diameter, and/or attached along a length of the tubular body. Sections of the micrograft or meltable/fusible sleeves of a braided polymer may also be heated and used to adhere bands or other radiopaque structures (components) to the micrograft. Bands or other radiopaque components can alternatively be attached by screwing into the coil windings inside the braid. The bands or other radiopaque components can either be self-expanding or non-self-expanding. When mated with the delivery wire and pusher catheter described below, they can serve to control micrograft linear movement relative to the wire.

As an alternative to the bands for providing radiopacity, a radiopaque agent as described above could be utilized which would allow complete visualization of the full length of the graft. Another way to provide visualization is the inclusion of a radiopaque coil or insert across the entire length of the inner lumen of the micro-graft. The addition of such coil would make the entire length of the graft radiopaque, however, preferably, to avoid such coil adding an unwanted increase to the structure's radial stiffness, and to minimize such stiffness while maximizing x-ray visibility, such coil may be wound using very thin wire typically not visible via fluoroscopy, but when coiled with sufficiently small pitch (spacing between each loop) it becomes increasingly dense and visible. Pitch of the coil may also vary to make some sections more radiopaque or flexible than others. The coil can be made of materials such as platinum, platinum-iridium, tantalum, gold, silver or other radiopaque materials used for medical device visualization. The coil can have a continuous diameter or variable diameter along its length, depending on use. The coil can also be used in combination with radiopaque bands, coatings or as a stand alone radiopaque solution. Insertion of such coils inside the micrograft may also reduce the amplitude of macro-crimps formed during crimping if desired, depending on radial apposition of coil to braid. It should also be noted that coils or other internal inserts may be partially visible through the braid wall depending on the amount of crimping.

If needed, a simple "J" shape can be heat set into tubular body 12 to aid with introduction into the aneurysm. Agents may also be added to the tube to aid in delivery and/or endothelial cell growth. For example, a hydrophilic coating can be applied to the surface of tubular body 12 to aid in delivery through a microcatheter or a swellable hydrogel infused with drugs can be added to provide medicinal treatment and additional filling of the aneurysm. Another example is a clotting agent which may be added to either slow or inhibit the clotting process or to promote clot formation. Bio-absorbable and bio-compatible fibrous elements such as Dacron (polyethylene terephthalate), polyglycolic acid, polylactic acid, a fluoropolymer (polytetrafluoroethylene), nylon (polyamide) or silk can also be incorporated into the braid, or to the surface, to enhance the ability of the tubular body 12 to fill space within the vasculature and to facilitate clot formation and tissue growth. Similarly, hydrogels, drugs, chemotherapy beads and/or fibers can be added to the inner diameter of tubular body 12 or infused into the walls, yarns, or fibers depending on specific use (for example embolic chemotherapy). On the finishing side of the micrograft (proximal end), a microcoil (not shown) may be added to provide a barrier between the aneurysm sac and the parent vessel. FIG. 1 can include similar features or functions as will be described below.

FIGS. 2A-2C illustrate a micrograft similar to micrograft 10 of FIG. 1 except having a larger diameter and thinner wall. FIG. 2A illustrates the thin walled micrograft 25 crimped in the process described above to forms peaks and valleys resulting in circumferential corrugations or folds. FIG. 2B is provided for illustrative purposes to highlight the peaks and valleys by stretching the tubular body. FIG. 2C shows a portion of the micrograft 25 in the bent position. In some embodiments, the micrograft is pre-set in this bend, e.g., a U-shaped configuration, to improve packing within the aneurysmal sac. As shown, due to the structure of the micrograft, when bent, it maintains its radius in the similar manner to a bent coil. (The micrograft would be delivered in a substantially linear position as described below). As shown, the compression and heat setting (crimping) process creates an "accordion like" structure with peaks 18' and valleys 20'. In FIGS. 2A-2C, the wall of the micrograft 25 is a fine braid, or textile structure, and will approximate a solid structure when placed in direct blood flow, causing high flow disruption. Another feature of the graft is its white color, which may vary depending on PET formulation and processing. If desired, colors other than white may be used to denote different body diameters or transitions in mechanical or therapeutic properties, for example.

Figure 4E:
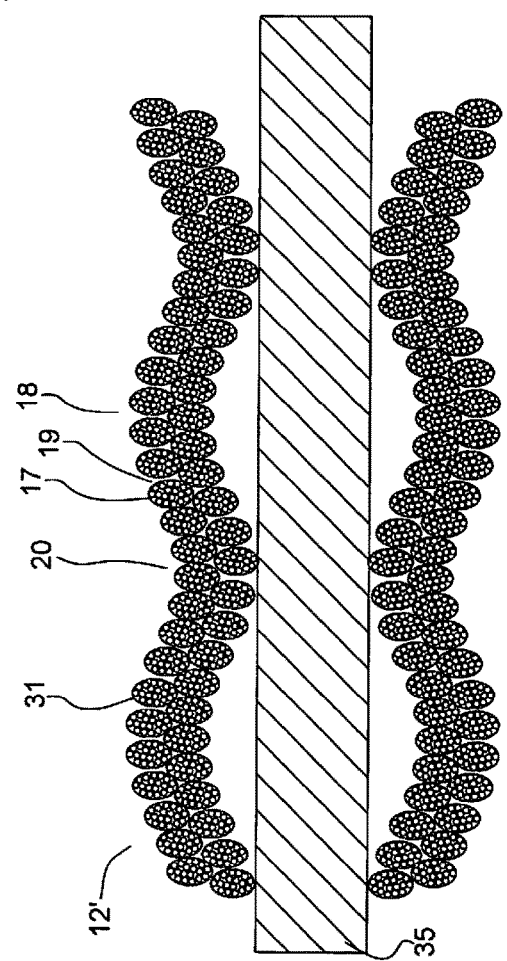
FIG. 4E is a cross-sectional side view of the micrograft of FIG. 4D after crimping.

FIGS. 4A, 4B, 4D and 4E show an alternative embodiment of the micrograft 10'. Micrograft 10' is similar to micrograft 10 as it formed from a braided tube 12' and has the same features and functions of tube 12 as well as can include any of the alternate constructions described herein. Thus, the various descriptions herein of the filaments, yarns, capillary effects, shape set, etc., are fully applicable to the micrograft 10' of FIG. 4A. However, micrograft 10' has a core element 27, preferably formed by a helical coil, having a lumen for blood flow in the aforementioned capillary effect. A tube 29, preferably composed of Nitinol, although other materials can be utilized, is seated within proximal coils of the tube 29, preferably screwed or twisted into the coil windings of the helical core element 27. The braid is melted onto tube 29, with region 24 showing the melted fibers, to attach the tube 29. Tube 29 has a deflectable tab 29a and a window 29b to receive a delivery wire as described below in conjunction with the delivery method. The tab 29a is biased to the aligned position of FIG. 4B and is moved to an angled position to receive the wire through the window 29b, the tab 29a providing an engagement/retaining structure for engagement with a wire of a delivery system described below. Braided tube or braid 12' is made up of yarns 31 each containing multiple fibers 33. When removed from the braider, the yarn(s) 31 of tube 12' will lay relatively flat with the fibers 33 bundled horizontal and spaced apart (see FIG. 4D showing tube 12' positioned over mandrel 35). FIG. 4E illustrates the braided tube 12' which has been crimped over mandrel 35 to create crimped braided tube 12' prior to formation into the structure of FIG. 4A. When the braid is fixed to the mandrel 35 at one or more points and a longitudinal force is applied to the braid, the fibers 33 in the yarn 31 will move closer together and bundle vertically creating micro peaks 17 and micro valleys 19 (between peaks 17) and corresponding macro peaks 18 and macro valleys 20 along the tube length creating a sinusoidal shape (FIG. 4E). (The peaks and valleys of the FIG. 1 embodiment disclosed herein can be formed in a similar manner). The extent of the peaks and valleys is dependent on the amount of force applied and the desired amount of softness. The tube can be completely crimped or selectively crimped at intervals along its length.

In the alternate embodiment of FIG. 4C, instead of a locking tab, a marker band 22' is attached to the tube to provide retention structure for engaging structure on the delivery wire. In all other respects, the micrograft of FIG. 4C is the same as the micrograft 10' of FIG. 4A and has therefore been labeled with the same reference numerals.

Figure 16B:
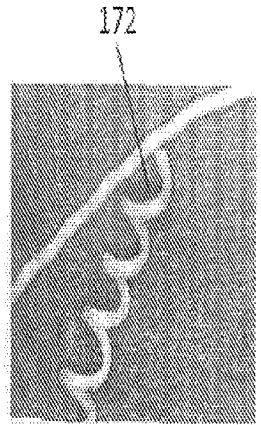
FIG. 16B is a photograph of a crimped micrograft braid alongside a crimped micrograft braid that has been heat set into a coiled shape in accordance with an embodiment of the present invention.

FIG. 3A illustrates another embodiment of an intra-aneurysmal micrograft. A variable stiffness micrograft 26 with tubular body 28 includes the same features and functions as described above with respect to FIG. 1, or its alternatives, e.g., multifilament yarns, capillary effects, etc. However, in this embodiment, the micrograft 26, after forming and crimping, is wound about a mandrel to form a secondary coil shape as shown. This is also shown in FIG. 16B wherein the micrograft 26 is pictured both after braiding and crimping (still straight) and after it's wound into a coil after formation of such braided and crimped structure. Other micrografts described herein, with the varying features described herein, can also be wound into a coil shape of FIG. 3A if desired. The tubular body 28 of micrograft 26 is composed of a variable stiffness braid having a proximal stiff section 30 and a distal flexible section 32, the varying stiffness achieved in the ways described above. Tubular body 28 also has a primary diameter D. A radiopaque band 36 can be provided to allow visualization under fluoroscopy and is shown in the approximate center of the braid where it transitions in stiffness. The radiopaque band 36 can alternatively be positioned in other locations and multiple bands can be provided. Alternatively, radiopacity can be achieved in the various ways described above.

Device 26 is shape-set with heat in a pre-biased (secondary) helical shape of FIGS. 3A (and 16B.) This is the delivered shape-set form of the device 26. This device may not have such pronounced peaks and valleys as micrograft 10 due to the stretching, bending and heating needed to form secondary shapes. However, the original crimping operation induces the desired properties and makes the micrograft more compliant. Partial stretching or partial un-doing of the crimping also results in a braided lumen that is more compliant radially for improved packing.

Although shown helically-shaped, device 26 can be shape set into any complex three dimensional configuration including, but not limited to, a cloverleaf, a figure-8, a flower-shape, a vortex-shape, an ovoid, randomly shaped, or substantially spherical shape. As mentioned earlier, a soft, open pitch coil can be added to the inner diameter of the braid to aid in visualization. If stiffness of such metal coil is sufficiently low, the secondary shape-set of the polymer braid will drive the overall shape of the device. In other words, the secondary shape of the braid molds the unshaped metal coil which normally shape sets at temperatures much greater than the glass transition temperature of polymers.

The micrograft 26 also has frayed end fibers 38 shown on one end of the device. These loose frayed fibers can alternatively be on both ends of the braid, if desired (other micrografts disclosed herein could also have such frayed ends). When these frayed ends come in contact with another braid within the aneurysm sac having the same feature, the mating ends act like Velcro, allowing the micrografts to interlock and move together. For delivery and introduction into catheter, device 26 would be elongated, e.g., moved to a substantially linear configuration, and inserted into a loading tube having an inner diameter of sufficient size to accommodate primary diameter D. An optional filament (not shown) may extend from the proximal end of the braid to allow pinching/anchoring of the micrograft between a stent or flow diverter and the parent vessel wall upon release to obstruct flow at the aneurysm neck. Packaging and delivery is discussed in detail below.

FIG. 3B illustrates another embodiment of an intra-aneurysmal micrograft. Sliced micrograft 40 has a tubular body 42 that can include the same features and functions as described above for the previous embodiments, e.g., multi-filament yarns, capillary effects, etc. Tubular body 42 has a longitudinal cut 44 and is shape set to expose its inner surface 46, thereby providing a flared distal end. Micrograft 40 is configured with a portion of the inner diameter exposed to maximize surface area constricted by flowing blood and to aid in movement with blood flow. Device 40 can include a proximal marker band 48 (or alternatively any of the other aforedescribed radiopaque features) for visualization. Holes 50 and 52, formed by laser cut or other methods, provide for communication with the blood. Micrograft 40 is particularly suited for placement at the neck of the aneurysm either manually with a delivery system or through movement with blood flow circulating within the aneurysm. Delivering micrografts 46 to an aneurysm may result in clogging at the neck/stent interface as they get caught up in exiting blood flow and accumulate at the aneurysm neck. This structure can also be a round tube, flattened tube, or other shape that is easily moved by blood flow.

The tubular bodies for the above embodiments have been described as crimped braided tubes, however, the tubes can be made using other manufacturing methods such as weaving, knitting, extruding, or electro-spinning. Structures can also be manufactured with alternating diameters or cross-sections, such as flat to round. In addition, the tube can be made from a rolled sheet or other material formed into desired tubular or substantially cylindrical structures. Structural flexibility can then be adjusted either by crimping or selective laser cutting, for example. If desired, the tubular body can also be flattened to create a thin walled tape or heat pressed to create oval sections.

Also, although crimping, or the use of axial/longitudinal compression and heat is described to produce crimps or peaks and valleys, other manufacturing methods of constructing peaks and valleys can be utilized to achieve similar effects. For example, a wire may be wound tightly around a braid placed on a mandrel. The gaps between windings will create peaks and when the assembly is heat set (with or without longitudinal compression) and the wire removed, valleys will be formed where the wire compressed the braid and peaks where the braid was exposed.

Figure 16C:
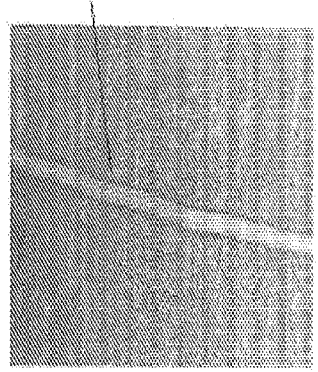
FIG. 16C illustrates a micrograft tubular body of the present invention partially filled with a fluid to illustrate the capillary effect.

FIGS. 16A through 16C and FIG. 17 illustrate a portion of micrograft 10 tubular body 12 constructed of 20 denier/18 filament polyester yarn. FIG. 16A shows examples of an uncrimped tubular body 171 alongside a crimped micrograft 10 tubular body 12 to illustrate the formed macro peaks and valleys. FIG. 16B shows a crimped tubular body alongside a tubular body that has been shape set into a helical coil 172 post crimping similar to FIG. 3A. FIG. 16C shows micrograft 10 that has fluid 174 which has been drawn into the micrograft via capillary action described earlier. FIG. 17 shows a tubular body with a marker band (stop collar) 22 attached to the body as in FIG. 1.

Turning now the delivery of the micrografts, several embodiments of delivery systems of the present invention are disclosed. Many of the delivery systems enable over the wire insertion which minimizes micrograft snaking inside the catheter as well as enables delivery of longer length micrografts. The delivery systems also enable retrievability of the micrograft after partial deployment, and in some embodiments, even after full deployment.

Turning to a first embodiment and with reference to FIGS. 5A-5D, an intra-aneurysmal micrograft delivery system is illustrated and designated generally by reference number 54. The delivery system is described below for delivering micrograft 10 but it should be understood that it (as well as the other delivery systems described herein) can be used to deliver any of the micrografts disclosed herein. Delivery system 54 includes a pre-loaded delivery wire 62 for carrying the micrograft and a pusher catheter 58, the pre-loaded delivery wire 62 positioned within the pusher catheter 58. Optionally the system could include a loading sheath similar to the loading sheath of FIG. 7 described below which is positioned thereover to retain the micrograft on the delivery wire 62. The individual components of the delivery system can be removed from the packaging during the procedure and assembled by inserting the delivery wire 62 proximally through the catheter 58 creating a junction 57 at the proximal end of the micrograft 10 and the distal end of the pusher catheter 58. Alternatively, they can be pre-packaged with the delivery wire 62 already positioned within the pusher catheter 58 and a protective loading sheath similar to the loading sheath of FIG. 7 positioned thereover to retain the micrograft 10 on the delivery wire 62. This delivery system may be used as a standalone delivery system to access the target anatomy, or with a microcatheter as described below. Any necessary flushing or coating activation can be done per physician's discretion prior to insertion into the patient.

Delivery wire 62 has micrograft 10 mounted thereon at region 56. Delivery wire 62 has a body with a length extending from proximal end 64 to distal end 66 can range between about 20 cm and about 400 cm, and more particularly between about 100 cm and about 300 cm, and even more particularly about 200 cm. Suitable diameters for the delivery wire 62 can range from about 0.0025 inches to about 0.040 inches, and more narrowly between about 0.002 inches and about 0.035 inches. The overall diameter of the delivery wire may be continuous, for example about 0.014" or the wire may taper from proximal to distal direction, for example about 0.007 inches to about 0.003 inches. Other sizes are also contemplated, dependent on the pusher catheter and/or microcatheter ID used for the procedure.

The distal portion 68 of the delivery wire 62 can include a coil and the very distal tip 66 of delivery wire 62 can be bulbous, of increased diameter, or fitted with a marker band or coil. The distal portion 68 of the delivery wire may be radiopaque as well as able to be shape set to aid in tracking, vessel selection, and intra-aneurysm maneuvering. For example the distal portion can be shape set to J-shape as in FIG. 11A described below. The delivery wire 62 may also be coated with a hydrophilic coating. The delivery wire 62 includes a retaining structure such as a tapered region to aid in retention of the micrograft 10 thereon. In alternative embodiments, to further aid retention, or if a delivery wire is utilized which does not have such retention structure such as a standard guidewire, then a protective loading sheath can be utilized. In another embodiment, the micrograft can be mounted using the micrograft introducer system 136 as described below with regard to FIG. 9.

Delivery wire 62 has a tapered region 70 (FIG. 5C) forming an engagement structure for mounting the micrograft 10. A proximal stop collar 22 is positioned over the tapered region 70. The stop collar 22 can be attached to the delivery wire 62 or alternatively and preferably form a retaining feature attached to an internal portion of the micrograft 10. In either case, the proximal end of the micrograft 10 is frictionally engaged and retained by the delivery wire 62. Micrograft 10 is mounted coaxially (and slidably) on wire 62 a distance L from the wire distal tip 66. The distance L is set by the proximal stop collar 22 which interacts with wire taper 70 as shown in FIG. 5C, or other hard stop on the wire (e.g., a marker band), and the overall length of the micrograft. For instance, longer micrografts may have a small distance L. In some embodiments, distance L may be zero and the hard stop may be on, inside or near the distal end of the micrograft 10 to interact with a bump, bulb or head (such has a head 184 of FIG. 5E described below) on the distal end of the delivery wire 62 to prevent the delivery wire 62 from passing through the distal end of the graft. In this instance, the distal tip of the micrograft 10 would be adjacent the distal end of the delivery wire 62 as in the embodiment of FIG. 5E.

FIG. 5C shows an enlarged cross sectional view of the proximal end of micrograft 10 with stop collar 22 engaging tapered region 70 of the delivery wire 62. The stop collar 22 as shown is in the form of a marker band to provide radiopacity for visualization. The wire taper 70 acts as a proximal stop to prohibit proximal movement of the micrograft 10 over the wire 62.

Other ways to couple or mate the micrograft and the delivery wire 62 are also contemplated. As mentioned earlier, proximal and distal Nitinol parts may be added to the micrograft as stops, or other parts and/or features (e.g., platinum marker band, notch, bump, etc.) can be added to the delivery wire to act as stops. In some instances, there may be no stop collar, the stop may be on the distal end of the braid (as mentioned above), the pusher catheter may act as the proximal stop, or the micrograft 10 can be sized to be free to slide across the entire length of the delivery wire, proximal to distal.

The pre-loaded delivery wire 62 may be supplied with one or more micrografts covered by a protective cover such as cover 92 of FIG. 7. This cover 92 has a tapered tip tapering to a smaller outer dimension for introduction into the lumen of a microcatheter or component thereof.

In some embodiments, more than one micrograft can be loaded on the delivery wire. They can be linked together on the delivery wire for delivery using one of the frayed, Velcro-like ends 38 described above with respect to FIG. 3 or inter-connected with assistance of the coaxial delivery wire running through them. That is, the device can in some embodiments be supplied pre-packaged with a plurality of micrografts in line along the delivery wire.

As mentioned above, the delivery system 54 includes a pusher catheter 58 having a lumen through which the delivery wire 62 extends. Pusher catheter 58 includes a catheter body 72 and a Luer lock 74. Catheter body 72 is preferably of a variable stiffness construction with a stiff proximal section, softer mid-section and still softer distal section. Individual sections of the catheter may be made up of polymer tubing with varying durometers to control stiffness, proximal to distal. The body may also be made from a variable stiffness, laser cut tube made of stainless steel alloy or Nitinol, for example. If polymer tubes are used, the catheter may also be a braid or a coil reinforced to keep from ovalizing. A lubricous liner made from materials such as PTFE, ePTFE, or FEP may also be added to the structure.

The outer diameter of the pusher catheter 58 is dimensioned to slide freely inside microcatheters with inner diameters ranging from about 0.008 inches to about 0.070 inches. Catheter body 72 can include a hydrophilic coating on its outer diameter for lubricity. The length of the catheter body 72 is preferably slightly shorter than the delivery wire 62 to allow proximal access to the delivery wire 62, i.e., holding the wire 62, while a micrograft (or multiple micrografts) is loaded on the distal end. The inner diameter of pusher catheter body 72 or the distal end is sized and shaped so that the micrograft 10 cannot be forced inside the catheter body 72 during distal advancement or proximal pulling of delivery wire 62. When loaded in the pusher catheter 58, the delivery wire 62 is preferably free to rotate and to move in a linear (back and forth) motion relative to the pusher catheter 58. Additionally, the pusher catheter 58 can be designed to accommodate delivery of stents or other devices or fluids to the target anatomy. In some embodiments, a clearance between an outer dimension of the delivery member and an inner dimension of the occluding device is substantially fluid-tight before delivery into the aneurysm but sufficient to enable slidable movement of the delivery member with respect to the occluding device.

At or near the distal end of pusher catheter body 72 is radiopaque marker band 76 which can be made of platinum/iridium and attached with adhesive, heat shrink tubing, a swaging process, or other known methods. Alternatively, the marker band can be placed inside the pusher catheter 58 with the delivery wire 62 passing through it. Other suitable radiopaque materials for marker band 76 include gold, silver, and radiopaque shrink tubes, or metal coils for example. A luer lock 74 can be positioned at the proximal end of the catheter 58 and attached to the luer lock 74 is a rotating hemostatic valve (RHV) 78 for saline, drug, contrast media or other fluid introduction though the inner diameter of pusher catheter 58. The RHV 78 also serves as a lock to stop relative movement between the pusher catheter 58 and the pre-loaded delivery wire 62 when the RHV 78 is tightened over (clamped onto) the wire. In some embodiments, the pusher catheter 58 can be delivered pre-packaged and sterile with an RHV as an accessory. In embodiments where a co-axial catheter stent delivery system is used, a pusher catheter may not be required as after stent deployment by the stent delivery catheter, the micrograft loaded delivery wire can be inserted into the stent delivery catheter to deploy micrografts.

As described earlier, the delivery wire 62 may be used as the primary access wire as in conventional guidewires. FIG. 6 illustrates an alternate design to the over-the wire pusher catheter, which is a rapid exchange pusher catheter designated generally by the reference number 80. The rapid exchange (RX) pusher catheter 80 has a catheter body 82 with marker band 76 at a distal end and a stiff push wire 84. Catheter body 82 will share many of the same features as the mid and distal section of catheter body 72 described above, including coating. The stiff pusher wire 84, which may taper, can be made of stainless steel alloy, Nitinol, or other suitable material. The pusher wire 84 may alternately be a hypo-tube, with or without laser cutting, or a wire featuring a non-round cross-section. The device may be supplied pre-packaged and sterile. In use, the RX catheter may be inserted over the delivery wire or guide wire before or after the aneurysm is accessed by the wire.

Figure 5A:
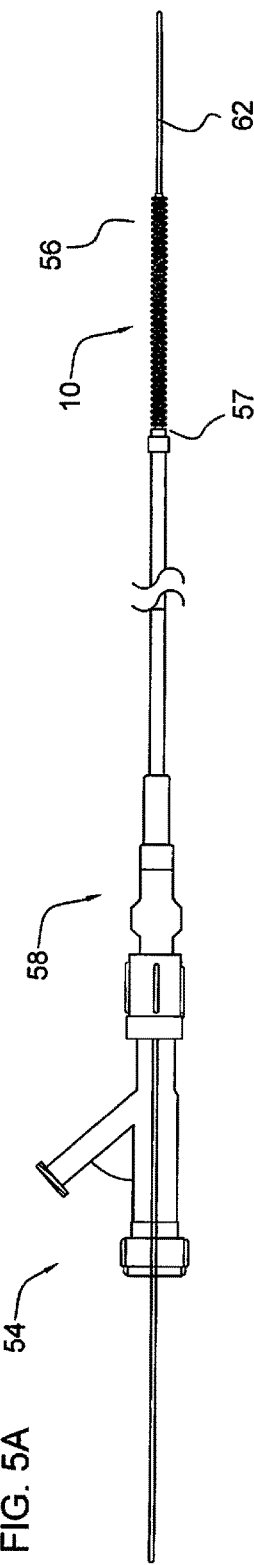
FIG. 5A is a side view of an intra-aneurysmal micrograft delivery system in accordance with an embodiment of the present invention.
Figure 5B:
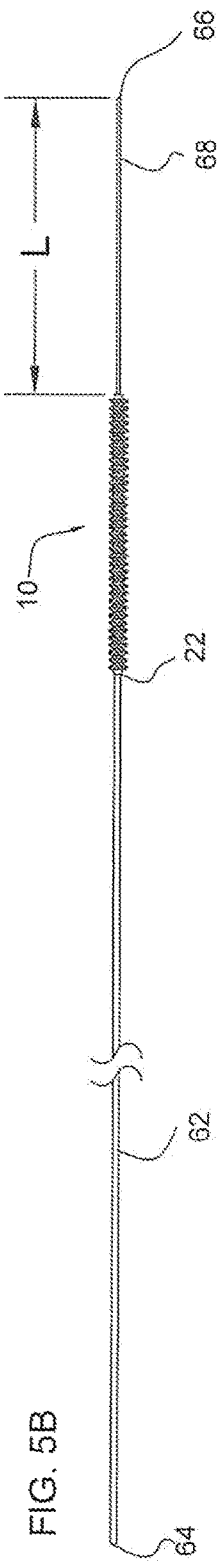
FIG. 5B is a side view of the delivery wire and mounted micrograft of FIG. 5A.
Figure 5C:
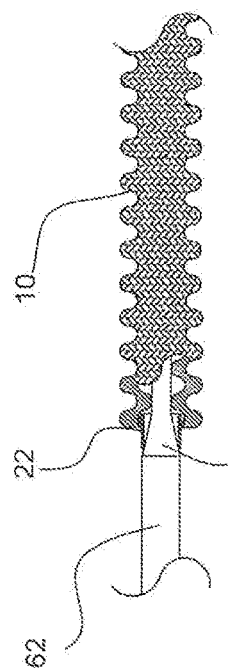
FIG. 5C is an enlarged partial cross-sectional view of the intra-aneurysmal micrograft of FIG. 5B showing the mating of the micrograft with the taper of the delivery wire.
Figure 5D:
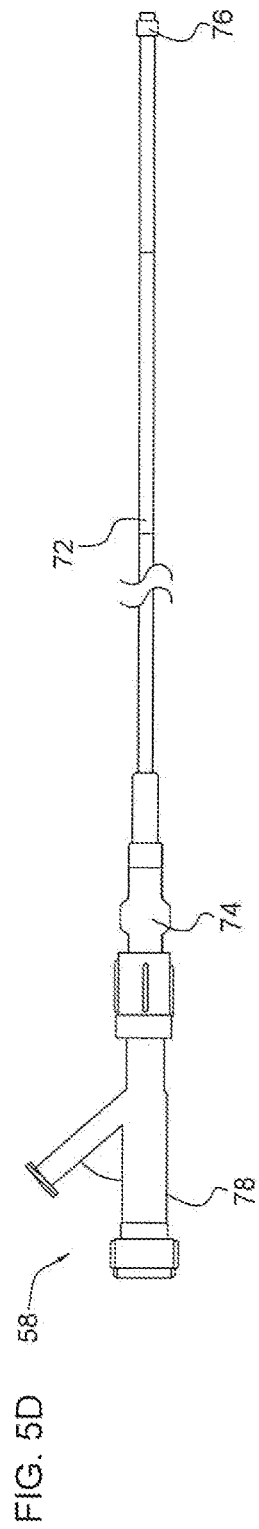
FIG. 5D is a side view of the pusher catheter of FIG. 5A without the delivery wire.
Figure 5E:
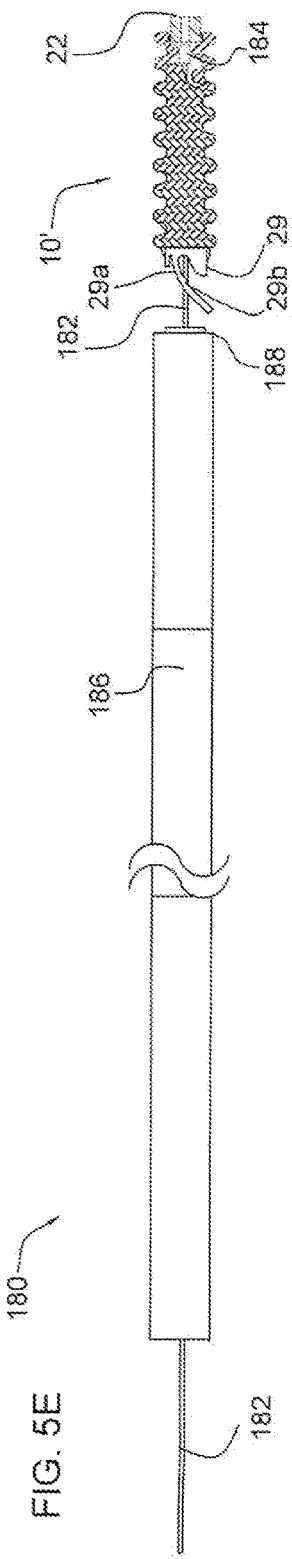
FIG. 5E is a side view of an alternate embodiment of the micrograft delivery system of the present invention.
Figure 5F:
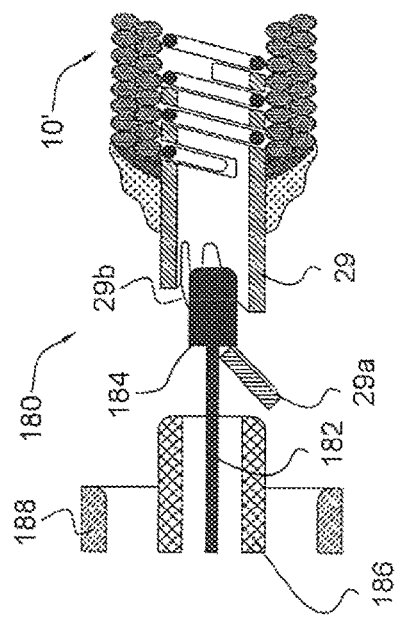
FIG. 5F is an enlarged cross-sectional view of a portion of the delivery system of FIG. 5E shown in the locked position.
Figure 5G:
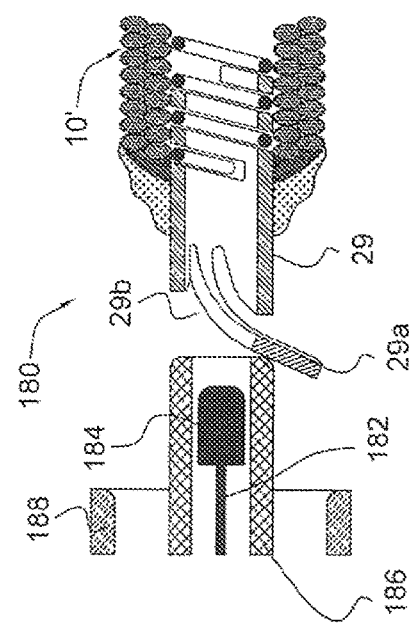
FIG. 5G is view similar to FIG. 5F showing the delivery system in the unlocked position.

FIG. 5E-5G illustrate a delivery system 180 for delivering the micrograft 10' of FIG. 4A. The delivery system has a pusher member 186 and delivery wire 182 with an enlarged head 184. In the initial position of FIG. 5E the tab 29a of micrograft 10' is bent downwardly and the delivery wire 182 passes through window 29b. The delivery wire 182 extends within micrograft 10' to the distal end of the micrograft 10'. In this position, head 184 engages the proximal edge of stop 22, e.g., distal marker band 22, on micrograft 10'.

The pusher member or catheter 186 has an internal stop 188 at its distal end to aid with pushing micrograft 10' as well as to inhibit movement of micrograft 10' into the pusher member's inner diameter. The pusher catheter 186 is shown by way of example without a luer attachment. Both the pusher catheter 186 and the delivery wire 182 may be constructed as previously described. In addition, although not shown, system 180 can include a protective introducer sheath similar to the loading sheath 92 of FIG. 7 to limit micrograft movement as well as to assist in micrograft introduction into a microcatheter.

In the initial position, tab 29a of micrograft 10' is bent downwardly and the delivery wire 182 passes through window 29b (FIG. 5E). The delivery wire 182, as mentioned above, extends inside the graft 10' such that enlarged head 184 comes into contact with the proximal edge of stop 22. Note, although the stop 22 is shown as open, it may be completely closed. Also, the stop may be excluded and the braid may be melted to narrow or close the distal end of the braid to prohibit the wire 182 from exiting. The use of a distal stop also serves the purpose of keeping the micrograft 10' in tension which aids in delivery by stretching and reducing the outer diameter of the micrograft 10'.

Figure 5H:
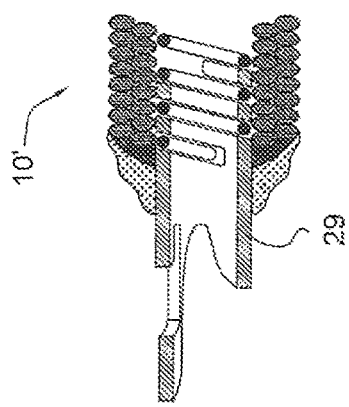
FIG. 5H is a view similar to FIG. 5G showing the delivery system withdrawn and the micrograft fully deployed.

The tab 29a provides a force against the delivery wire 182 to retain the micrograft 10' on the wire 182. Upon delivery, the wire 182 is retracted to the position of FIG. 5F where delivery wire enlarged tip 184 engages the tab 29a. Up to this position the micrograft 10' can be retrieved from the aneurysm and/or maneuvered therein. Next, pusher catheter 186 is advanced (or wire tip retracted) to force the tab 29a to the position of FIG. 5G, therefore enabling full retraction of the enlarged head 184 of the delivery wire 182 through window 29b for release of the micrograft 10' from the delivery wire 182. FIG. 5H shows the tab 29a returned to its original position longitudinally aligned with the micrograft 10' after retraction of the delivery system.

FIG. 7 illustrates another embodiment of an intra-aneurysmal micrograft delivery system generally referred to by reference number 86. Delivery system 86 comprises a pusher wire 88 and a loading tube 92. Pusher wire 88 includes an elongate tapering flexible wire that can be made from stainless steel, or alternatively, Nitinol, plastic or other inert or biocompatible material or combination thereof.

Although shown as a wire, the pusher wire can alternatively be a hypo-tube with a Luer lock.

At the distal end of pusher wire 88 are expanding grasper members or arms 94, 98. Although there are four grasper arms in this design, more or less than four arms may be used. The arms 94, 98 can be made of shape set shape memory material such as Nitinol, spring tempered stainless steel, radiopaque metal, or other suitable material. The arms 94, 98 can alternatively be manufactured from a metal or elastic tube which is laser cut to create deflectable arms. Attached to the distal end of one or more of the grasper arms are radiopaque bands (see labeled bands 102, 106, and 108; the fourth band not shown since the fourth arm is not shown). The bands can be attached with glue, solder or other methods. The proximal ends of the arms are attached to the pusher wire 88 by a coil 110 which can be made of wound stainless steel or platinum iridium, for example. Attachment methods may include gluing, welding, or soldering. The use of the grasping arms has the advantage of enabling grasping of the micrograft after full deployment to retrieve/remove the micrograft or to maneuver/reposition the micrograft within the aneurysm as described below.

The pusher wire 88 has a length (including arms) between about 20 cm and about 400 cm, more narrowly between about 100 cm and about 300 cm, for example about 200 cm. Suitable diameters for the pusher wire 88 can range from about 0.006 inches to about 0.040 inches, more narrowly between about 0.008 inches and about 0.035 inches. The overall diameter of the pusher wire 88 may taper from proximal to distal, for example about 0.014 inches tapering to about 0.003 inches. The pusher wire 88, either in part or whole, may be coated with a hydrophilic or PTFE coating for lubricity Loading tube 92 is made of either metal or plastic and preferably has distal taper 112 for mating with a microcatheter Luer taper. The loading tube 92 preferably has a length sufficient to cover the entire micrograft 90 and at least a portion of coil 110. The inner diameter of the loading tube 92 is preferably close to the inner diameter of the microcatheter to which it will mate. A range for the inner diameter may be between about 0.008 inches and about 0.070 inches. The loading tube may have a crimp or other fixation method to prevent relative movement to the pusher wire 88. If used on a structure having a Luer or other attachment on its proximal end, the introducer may have a lengthwise slit to aid in removal (i.e., peel-away).

One way to load micrograft 90, which has proximal band 114, e.g., a marker band, is to position the loading tube 92 on pusher wire 88 just proximal to the two pair of grasper arms 94, 98 so that the arms are in their normal expanded position. The band 114 on micrograft 90 is then positioned between bands 102 and 104 (one on each arm of arms 94) and bands 106 and 108 of arms 98. Note to achieve axially spaced bands, the arms 94 can be shorter than arms 98 so the bands 102, 104 are proximal of bands 106, 108, or alternatively, the arms 94, 98 can be the same size and bands 102, 104 can be placed on a more proximal position of arms 94 (spaced from the distal end) while bands 106, 108 can be placed on a distal end or more distal position of arms 98. The loading tube 92 is then advanced forward (distally) compressing the pusher arms 94, 98 to a collapsed or compressed position to engage (grasp) the band 114 to retain the micrograft 90 in place. Thus, band 114 forms an engaging or retention structure for engagement by the pusher (delivery) wire 88 to retain the micrograft 90 on the wire 88.

Note micrograft 90 is similar to micrograft 10 except for the proximal band 114 which is positioned around a portion of the braided structure.

Note alternatively, instead of the micrograft having a single proximal marker band, it may have two proximal bands where the bands of the pusher wire sit to create a lock when compressed inside the lumen of the loading tube. Alternatively, a micrograft with an internal coil may have proximal coil windings spaced to have a gap that allows radial compression and grasping by the bands of the pusher wire.

FIG. 8 illustrates yet another embodiment of an intra-aneurysmal micrograft delivery system generally referred to by reference number 116. Delivery system 116 is a neurovascular stent-graft kit that comprises a pusher wire 118 with distal band 120, stent or flow diverter 122 with proximal arms with bands 124 and 126 and distal arms with bands 128 and 130, micrograft 132 with proximal band 134, and loading tube 133. The micrograft 132 is locked proximally by the stent 122 and stent bands 128 and 130 and loading tube 133. Stent or flow diverter 122 is in turn locked to pusher wire 118 using a similar locking concept as bands 124, 126 are blocked by band 120. The number of arms for both locking systems may vary to be more or less than two. Delivery system 116 can also be configured to have a through lumen for guidewire delivery.

The delivery system 116 provides a single delivery system that can deliver a micrograft and a stent that can be combined on site to form a neurovascular stent-graft. Alternately, the stent may be permanently attached to the pusher wire and acts as a temporary stent to push grafts into the aneurysm.

Figure 9:
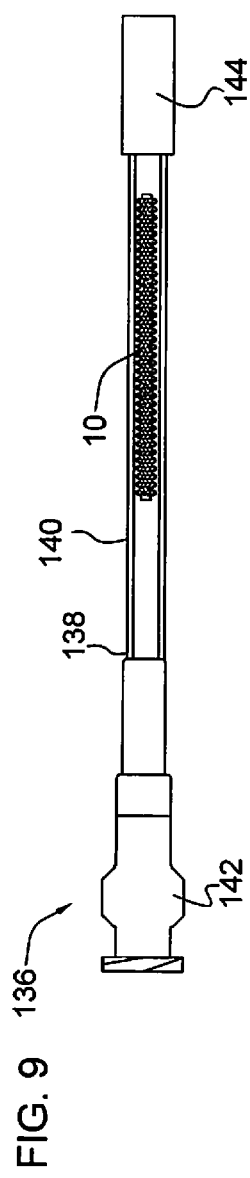
FIG. 9 is a side view of an intra-aneurysmal micrograft introducer system in accordance with another embodiment of the present invention.

FIG. 9 illustrates a micrograft introducer system 136 which may be used to mount micrografts on a delivery wire or on a guidewire before or during a medical procedure. Micrograft loader introducer system 136 comprises introducer sheath 138 loaded with micrograft 10. The introducer sheath includes tubular body 140, Luer lock 142, and stop tube 144. Tubular body 140 can be made of metal, plastic or a combination of materials and sized with an inner diameter between about 0.008 inches and about 0.070 inches and a length that covers all or substantially all of the micrograft 10. The distal tip of the tubular body 140 may be straight or tapered to help in micrograft introduction and handling. The Luer lock can be attached to an RHV such as RHV 78 of FIG. 5D for the introduction of fluid such as, saline or contrast media, guide or delivery wires and pusher catheters. The stop tube 144, which is optional, has a through lumen and can be made of plastic or metal and may have a taper proximal to distal. The purpose of the stop tube is to prohibit the micrograft from exiting the tubular body 140 prior to loading and may be removed prior to insertion.

Although FIG. 9 shows only one micrograft, multiple micrografts may be delivered in a single introducer sheath. They may be free to move relative to one another or linked together using the frayed ends method, for example, as described above. Micrografts having secondary shapes will generally be linear or straight when loaded into the introducer sheath such that they are concentric.

Introducer system 136 is delivered pre-packaged and sterilized. Once opened, an RHV and syringe may be attached to the Luer to introduce fluids. A delivery wire or guidewire may be pushed into the introducer sheath 138 to mount the micrograft(s) on the wire or alternatively the introducer sheath 138 may be mated with the proximal end of the microcatheter and the micrografts may be pushed proximally through the sheath 138 and into the microcatheter using a pusher catheter, with or without a wire, or with a commercially available pusher wire.

The micrografts disclosed herein can be preset to a non-linear configuration and advanced to the aneurysm in a substantially linear configuration and then return to the same non-linear configuration or different non-linear configuration when delivered into the aneurysm, depending on the space within the aneurysm.

Figure 10:
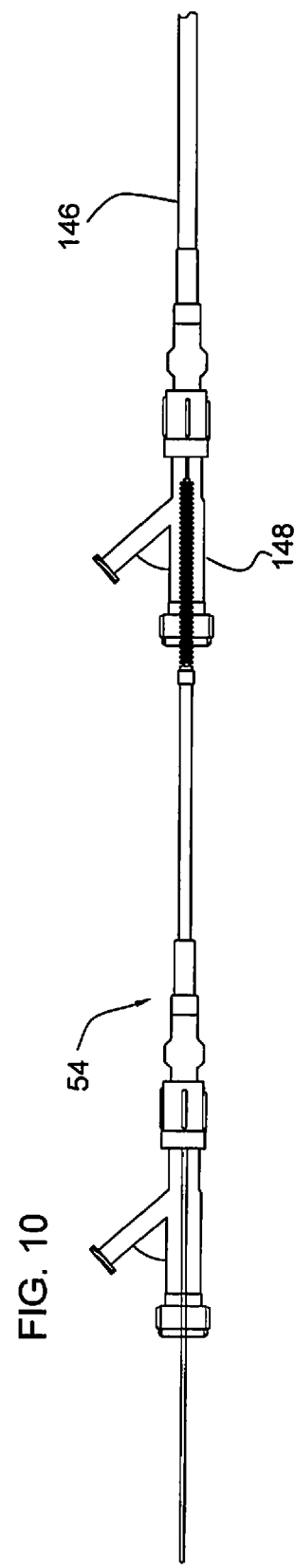
FIG. 10 is a side view illustrating the loading of an intra-aneurysmal micrograft delivery system of FIG. 5A into a microcatheter.

FIGS. 10 through 11F show the preferred method of using intra-aneurysmal micrograft delivery system 54 of FIG. 5A to deploy micrograft 10 of FIG. 1. (Other micrografts described herein can be inserted in a similar fashion). The micrograft delivery method, as well as the "viscosity lock" function (described below) are depicted in flow chart form in FIGS. 18 and 19. Before implantation, the delivery system may be prepared prior to patient insertion as described above or as preferred by the physician.

Typical intracranial aneurysm access requires inserting a guide catheter into the femoral artery and then tracking a microcatheter in combination with a primary guidewire through the vasculature until the aneurysm site is reached. Once there, the primary guidewire is removed and replaced with an embolization system. FIG. 10 shows micrograft delivery system 54 of FIG. 5A being inserted as a unit into the proximal end of microcatheter 146 (with attached RHV 148), the microcatheter 146 having been inserted through the guide catheter and advanced to the aneurysm site and the primary guidewire removed.

Figure 11A:
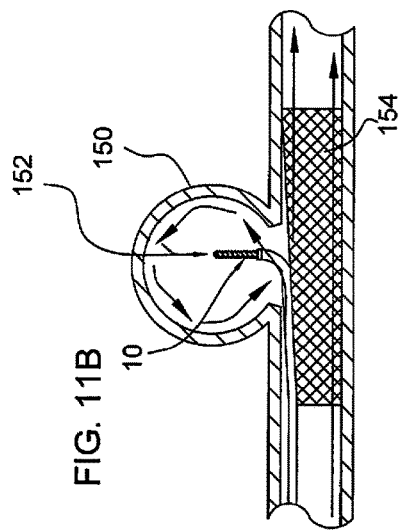

FIG. 11A illustrates the distal tip 66 of delivery wire 62 exiting microcatheter 146 that has been positioned inside aneurysm 150 and is held in place using a "jailing" stenting technique, surrounded by blood 152. Jailing refers to the use of a stent or flow diverter 154 to pin the distal tip of the microcatheter between the parent vessel intima and the stent or flow diverter 154, so that the microcatheter tip is held within the aneurysm and delivered occluding devices, e.g., micrografts 10, are kept out of the parent vessel lumen. Other techniques that may be used instead of jailing include temporary stenting and balloon remodeling. It is also contemplated that the micrografts of the present invention be deployed without the use of such parent vessel support (stent or flow diverter) devices.

Figure 11B:
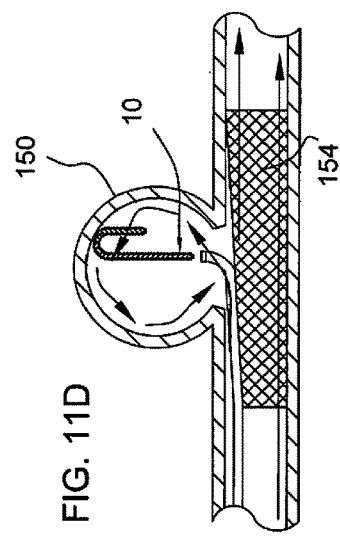

Once the system is in place as shown in FIG. 11A, the exposed delivery wire tip 66, which has the pre-bent curve as shown, is slowly retracted into the micrograft 10. The retraction can be done in incremental steps of a few centimeters or completely until it reaches a location at, or near, the pusher/micrograft juncture 57 (see FIG. 5A). As the delivery wire 62 is retracted proximally toward junction 57, blood 152 will be drawn into the micrograft's inner lumen to fill the volume previously occupied by the delivery wire 62, as depicted in FIGS. 11B and 11C. This filling action occurs through a combination of the unique internal capillary features of the micrograft described earlier and due to a syringe-like "piston" effect of the receding wire.

Figure 11D:
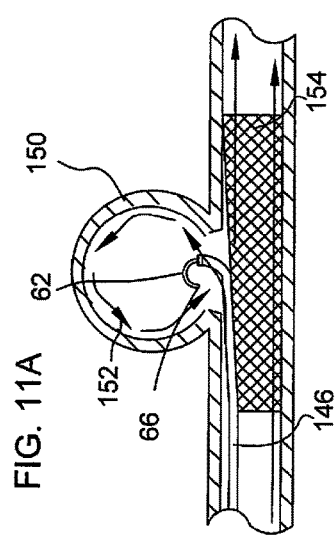
Figure 11C:
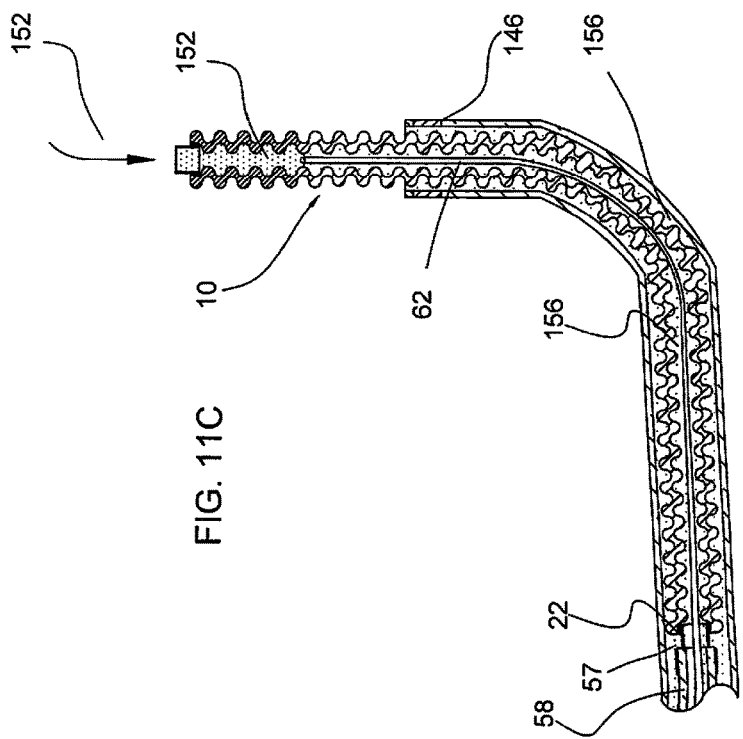

With the delivery wire 62 pulled back and in some embodiments pulled back to a locked position against tab 21a, as in the embodiment of FIG. 5F, the micrograft 10 can be pushed forward off the wire 62 and into the aneurysm as illustrated in FIG. 11D using the pusher catheter 58 (FIG. 5A) as it is advanced distally and engages the proximal end of the micrograft 10. Note that if the delivery system does not feature a mechanical lock physically connecting the pusher catheter 58 or delivery wire 62 to the micrograft 10, the micrograft 10 may still be retrieved due to a "viscosity lock" (described below) that is formed inside the microcatheter 146, between the delivery system components and micrograft, once surrounded by a viscous liquid (e.g., blood). This lock allows the micrograft 10 to be advanced and retracted while the proximal end of the micrograft 10 remains inside the lumen of the microcatheter 146 until desired placement is achieved.

Micrograft 10 is pushed forward by pusher catheter 58 and the wire 62 can be pulled further proximally to junction 57, if it is not positioned there already. Once the wire 62 reaches junction 57, the inner lumen of the micrograft 10 will be completely filled with blood 152 that displaces the wire 62 and with any liquid that has been present (e.g., contrast). Since blood now fills the inside lumen of the micrograft 10 and has already permeated the braided walls via the aforedescribed capillary action, the saturated device is composed in part of the patient's blood. Thrombosis and cell in-growth through the microporous yarns will be accelerated as the blood becomes trapped and stagnant within the micrograft (implant) after delivery.

Note that blood can enter the lumen of the micrograft 10 through a distal opening of the lumen and/or through other intermediate or proximal regions of the lumen spaced from the distal end as blood is absorbed through the braided structure. As blood enters such intermediate or proximal regions, it spreads in various dimensions as well as is directed proximally due to the aforedescribed capillary action.

As the micrograft 10 is deployed into the aneurysm, it will take on any preset secondary shapes and random shapes due to contact with aneurysm walls or the stent/flow diverter 154, as shown in FIGS. 11D and 11E. That is, in these Figures, micrograft 10 has a pre-set U-shape as shown, however, this shape can change as it contacts the aneurysm wall and/or stent 154. If the proximal end of micrograft 10 remains inside the microcatheter, the micrograft 10 can be retracted and repositioned at any time prior to full deployment as described above. The micrograft 10 will be fully deployed and disengage from the delivery system once the distal tip of the pusher catheter 58 reaches or exits the distal end of the microcatheter 146. FIG. 11E shows an enlarged cross section of the fully deployed pre-shaped blood filled micrograft 10 of FIG. 11D.

After the first micrograft 10 has been deployed, the delivery wire 62 and pusher catheter 58 are removed and, if needed, another micrograft 10 is loaded on the wire 62 or a new delivery system is opened, and the deployment process is repeated as described above. Multiple micrografts can be deployed by repeating the above steps until the aneurysm is sufficiently packed (per physician discretion) as shown in FIG. 11F. If needed, the microcatheter tip or the delivery wire 62 can be used in between packing or during packing to move or compress micrografts within the aneurysm. Once the aneurysm is sufficiently packed, the microcatheter is removed and the stent or flow diverter 154 continues to expand to cover the neck of the aneurysm 158 to thereby block exit of the micrografts 10 from the aneurysm sac. Together, micrograft 10 and stent or flow diverter 154 form neurovascular stent-graft 160, as shown in FIG. 11F.

As mentioned above, delivery system 54 features a temporary liquid seal or "viscosity lock" effect inside the microcatheter which allows limited retrieveability (push/pull) of the micrograft during placement. The "pull" of the lock is generated by the tip of the pusher catheter 58, which creates a syringe-like "piston" within the fluid-filled microcatheter 146. Functionality of this lock is dependent on clearances between the microcatheter lumen, proximal micrograft 10 body, adjacent pusher 58 tip, the delivery wire 62, as well as the viscous and cohesive properties of the fluid medium.

Figure 19:
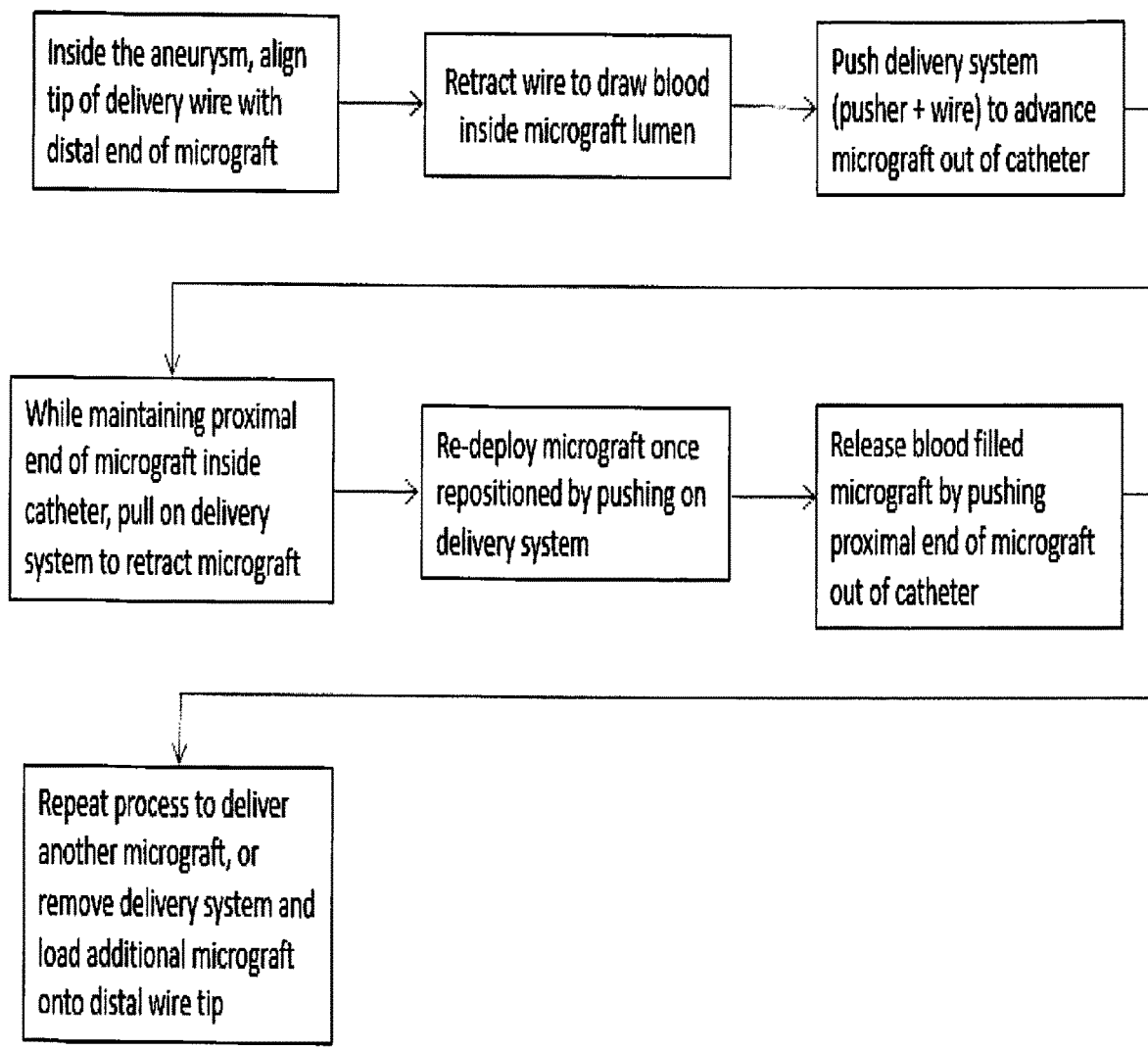
FIG. 19 is a flowchart summarizing viscosity lock function in accordance with an embodiment of the present invention.

The flow chart of FIG. 19 describes the steps of the viscosity lock function which are as follows:
1) Inside the aneurysm, align tip of delivery wire 62 with distal end of micrograft 10.
2) Retract wire 62 to draw blood inside micrograft lumen up to the pusher junction 57.
3) Push delivery system (pusher 58+wire 62) to advance micrograft 10 out of catheter 146.
4) While maintaining proximal end of micrograft 10 inside catheter 146, pull on delivery system to retract micrograft 10.
5) Re-deploy micrograft 10 once re-positioned by pushing on delivery system.
6) Release blood filled micrograft 10 by pushing proximal end of micrograft 10 out of catheter 146.
7) Repeat process to deliver another micrograft 10, or remove delivery system and load additional micrograft 10 onto distal wire tip.

In order for the viscosity lock to work, viscous liquid (i.e., blood) must fill the microcatheter past the micrograft/pusher junction. Once viscous fluid fills the micrograft(s) 10 and gaps around the pusher junction 57, it acts as a "gasket", or a seal, around the pusher/micrograft junction 57 during any displacement (i.e., as the pusher is retracted). The action of pulling the pusher 58 (i.e., the piston) adjacent to the proximal end of the micrograft now creates a low pressure volume. This causes the micrograft(s) 10 suspended in blood to get suctioned and retract within the microcatheter 146.

The micrograft 10 may also be retractable if the delivery wire distal tip 66 is pulled back proximal to the distal tip of pusher 58 or removed completely. High friction or pull resistance are more likely to break the "viscous lock", so the preferred application for this retrieval method is with shorter, lower friction devices or where minimal tortuosity and resistive forces are involved.

In some embodiments of the micrograft delivery system, a pusher wire or delivery wire may not be present inside the micrograft lumen and internal filling of the micrograft with blood will be induced by pressure from the patient's circulatory system or via capillary forces. Capillarity can be achieved by the micrograft having appropriately sized inner diameter or pores, as described earlier. Hence, the absorption of blood into micrograft depicted in FIG. 11C can occur upon contact with blood even if delivery wire or external force is not used to draw blood in.

FIGS. 12A through 12C show directed delivery of micrograft 10 of FIG. 1 inside an intracranial aneurysm. Other micrografts described herein can be delivered in a similar manner. Unlike micrograft delivery described in FIGS. 10 and 11A-11F above, in the embodiment of FIGS. 12A and 12B, the shaped delivery wire 62' remains in the aneurysm so that the micrograft deployment can be directed to a targeted location (neck) within the aneurysm sac. FIG. 12A illustrates a distal tip 66' of delivery wire 62' that has been shape set in a "J" and deployed so that the "J" points at the stent or flow diverter 154 covering the neck of the aneurysm. As the pusher catheter 58 is advanced distally, the micrograft 10 will deploy and follow along the delivery wire 62' in a direction denoted by arrow 162 towards the stent or flow diverter 154.

FIG. 12B illustrates a delivery wire 62' that has been shape set with a "J" and advanced into the dome of the aneurysm. As the micrograft 10 is advanced it will follow the curvature of the wire 62' in a direction denoted by arrow 164.

FIG. 12C illustrates that the microcatheter 146 can be used to direct micrograft deployment within the aneurysm. The delivery wire has been pulled back into microcatheter 146 which is seated in the neck of the aneurysm 158. As the micrograft 10 is advanced it will follow the direction denoted by arrow 166. The tip of the microcatheter 146 can be curved to direct the micrograft 10. When the micrograft 10 encounters barriers, such as the aneurysm wall, it will easily change direction as depicted.

Figure 13:
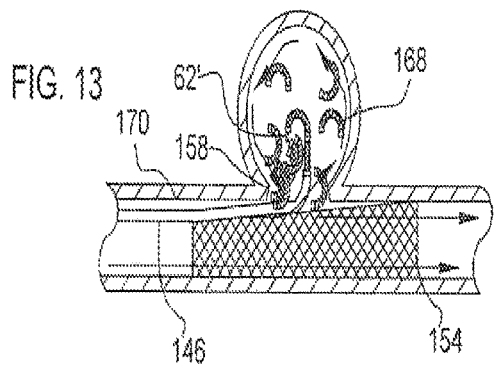
FIG. 13 illustrates delivery of smaller length flow directed intra-aneurysmal micrografts into an intracranial aneurysm in accordance with another embodiment of the present invention.

FIG. 13 illustrates the deployment of flow directed micrografts 168 using intra-aneurysmal micrograft delivery system 54 with delivery wire 62' having a "J" form at its tip and extending from microcatheter 146. Micrografts 168 can have the same structure as other micrografts described herein. Flow directed micrograft 168 can be any length, but shorter lengths such as about 2 mm to about 5 mm are utilized in this embodiment so as to move with blood flow. Since the flow directed micrografts 168 tend to be shorter than micrografts configured to fill the aneurysm, many more flow directed micrografts can be loaded onto the delivery wire and consecutively deployed, as illustrated in FIG. 13. Micrograft 168 has been shape set into a "C" shape, however, other shapes are also contemplated as discussed above.

As each micrograft 168 is advanced distally off the delivery wire 62', it will be caught up in blood flow exiting the neck of the aneurysm. Due to the stent or flow diverter 154 blocking the neck 158, micrograft 168 will be restricted from exiting into parent vessel 170. When a sufficient amount of micrografts 168 are introduced into the aneurysm, the micrografts will pile up and clog or create a localized graft at the stent/flow diverter and neck interface. Over time, thrombus will form above the clog to aid in closing off the aneurysm. The smaller, shorter micrografts are intended to provide a more complete obstruction or fill voids at the aneurysm neck.

Figure 14:
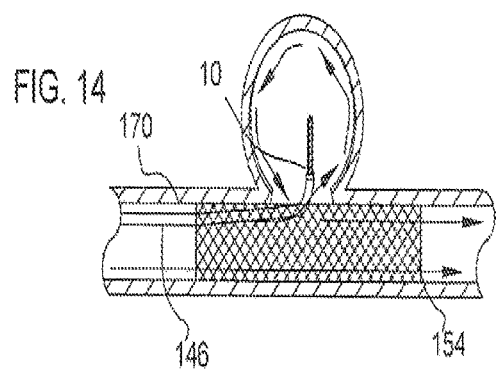
FIG. 14 illustrates delivery of the delivery wire carrying the intra-aneurysmal micrograft through cells of a stent or flow diverter into an aneurysm in accordance with another delivery method of the present invention.

FIG. 14 illustrates microcatheter 146 positioned inside the parent vessel 170. This embodiment differs from the previous embodiments in that instead of extending in the space between the stent 154 and parent vessel 170, the microcatheter 146 extends through the struts or pores of stent or flow diverter 154. In all other respects, the system is the same as that of the aforedescribed systems. Note micrograft 10 is shown exiting the microcatheter 146 into the aneurysm. Longer length or shorter length micrografts can be delivered.

As discussed earlier, the delivery wire 62 can be a guidewire. Therefore, if desired, the micrograft delivery system with guidewire can be loaded into the microcatheter prior to catheter placement. The entire assembly, microcatheter and micrograft delivery system, can then be tracked to the aneurysm site using the delivery system's guidewire as the primary tracking wire. Alternately, the guidewire and microcatheter can be tracked to the aneurysm site and rapid exchange catheter, e.g., pusher catheter 80 of FIG. 6, can be advanced subsequently.

Figure 15:
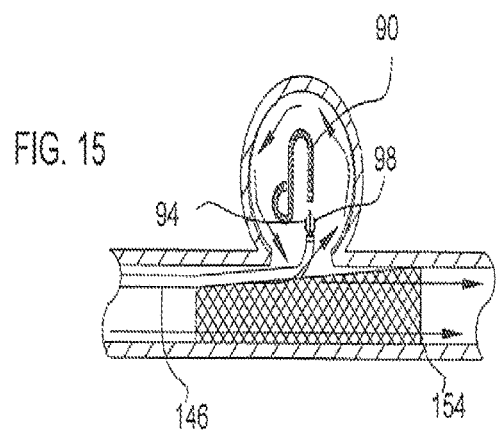
FIG. 15 illustrates delivery of an intra-aneurysmal micrograft into an aneurysm using a delivery wire with the arms of FIG. 7.

FIG. 15 illustrates the distal end of intra-aneurysmal micrograft delivery system 86 of FIG. 7 deploying micrograft 90. Micrograft 90 has been released from arms 94, 98 and has assumed a pre-biased (pre-set) shape. As noted above, the micrografts can be pre-set to a variety of configurations and the shapes illustrated in the drawings are provided by way of example. If desired, the micrograft 90 can be retrieved by capturing a portion of the structure between arms 94, 98, and advancing the microcatheter 146 over the arms to compress the arms. Alternatively, the delivery arms 94, 98 can be used to compress or move the micrograft around the aneurysm to aid in packing.

Figure 18A:
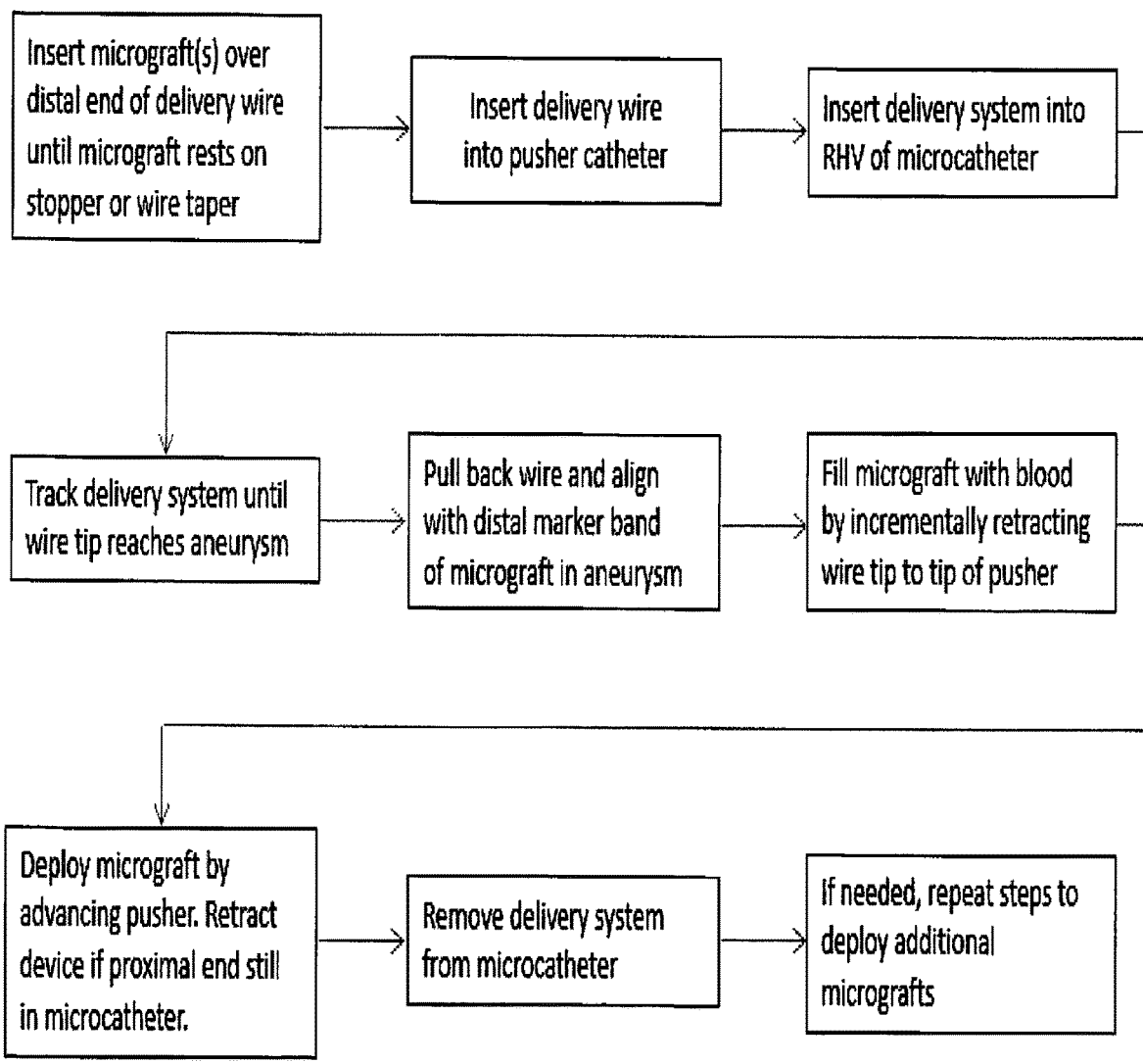
FIGS. 18A and 18B are flowcharts summarizing alternate methods of placing and deploying a micrograft of the present invention.

FIG. 18A provides a flow chart for one method of placing a micrograft of the present invention. This method utilizes the delivery system of FIGS. 5A and 5C. The steps include:
1) Insert micrograft(s) over distal end of delivery wire 62 until micrograft rests on stopper or wire taper 70.
2) Insert delivery wire 62 into pusher catheter 58.
3) Insert delivery system into RHV 78 of microcatheter.
4) Track delivery system until wire tip 66 reaches aneurysm.
5) Pull back wire 66 and align with distal marker band of micrograft in aneurysm.
6) Fill micrograft with blood by retracting wire tip 66 into the micrograft.
7) Deploy micrograft by advancing pusher 58. Retract device if proximal end still in microcatheter.
8) Remove delivery system from microcatheter.
9) If needed, repeat steps to deploy additional micrografts.

Figure 18B:
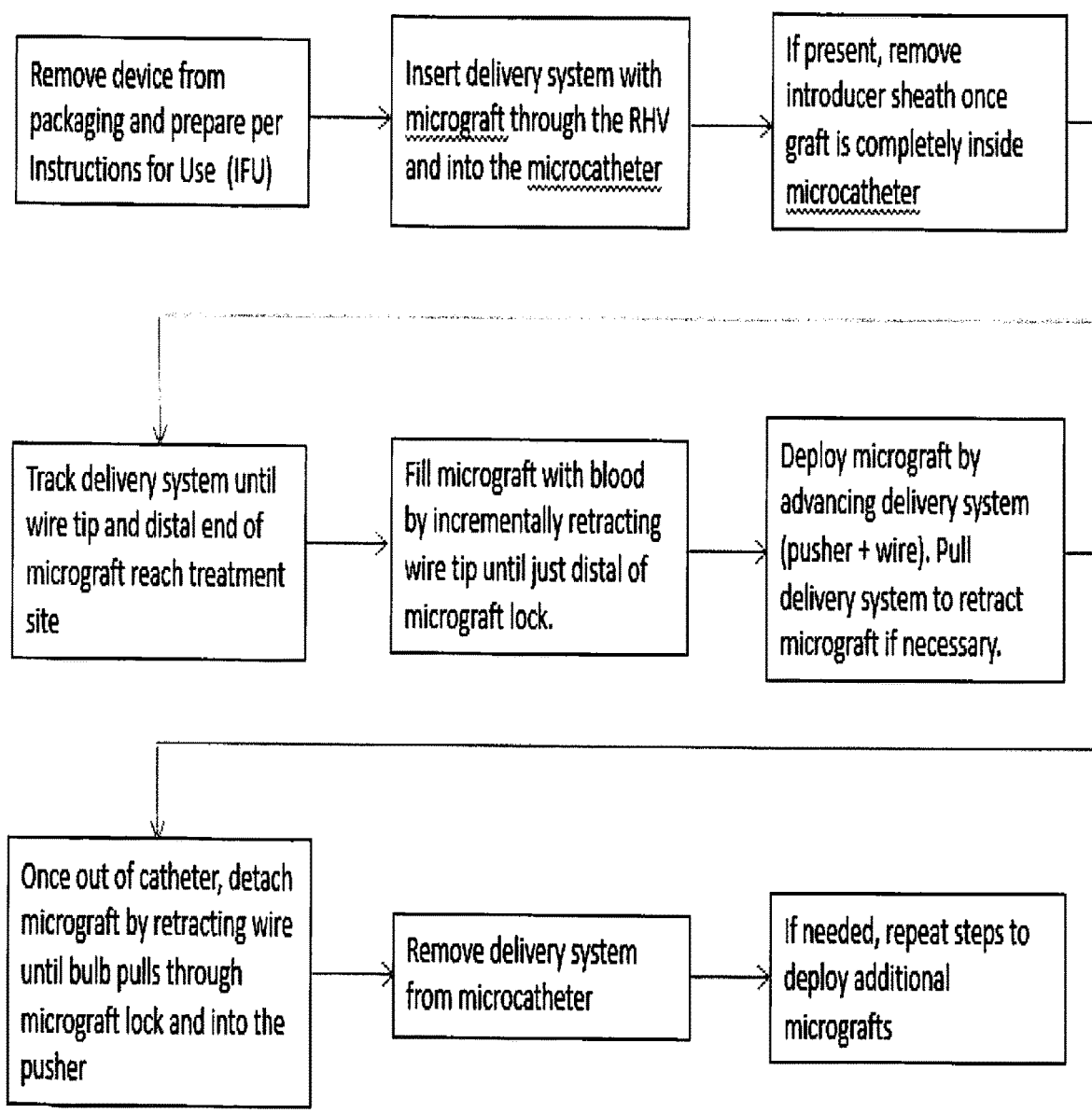

FIG. 18B provides a flow chart for another method of placing a micrograft of the present invention. This method utilizes the same delivery system of FIGS. 5E-5H. The steps include:
1) Remove device from packaging and prepare per Instructions for Use (IFU).
2) Insert delivery system with micrograft into microcatheter RHV.
3) If present, remove introducer sheath once micrograft is inside microcatheter.
4) Track delivery system until wire tip 184 and distal end of micrograft reach the treatment site.
5) Fill micrograft with blood by incrementally retracting wire tip 184 just distal of the micrograft lock (tab 29a).
6) Deploy micrograft by advancing delivery system (pusher 186 and wire 182). Pull delivery system to retract micrograft if necessary.
7) Once out of microcatheter, detach micrograft by retracting wire 182 (or advancing pusher) until wire bulb 184 pulls through micrograft lock (tab 29a) and into the pusher 186.
8) Remove delivery system from microcatheter.
9) If needed, repeat steps to deploy additional micrografts.

Note the delivery systems and occluding devices (micrografts) disclosed herein have been described for use with treating intracranial aneurysms. It should be appreciated that the delivery systems and occluding devices (micrografts) can also be utilized for treating aneurysms in other regions of the body or for treating other vasculature or for treating non-vascular diseases.

Note the delivery systems disclosed herein can be utilized to deliver the various micrografts disclosed herein and specific micrografts discussed in conjunction with specific delivery systems are provided by way of example.

The above delivery systems and concepts are preferred ways to deliver the intra-aneurysmal micrograft. The micrograft however may alternatively be constructed to mate with other microcoil delivery systems that provide a timed and controlled release, e.g., electrolytic detachment as described in U.S. Pat. No. 5,354,295 and its parent, U.S. Pat. No. 5,122,136, both to Guglielmi et al., interlocking ball and key way as described in U.S. Pat. No. 5,261,916 to Engelson, and pusher with mating ball configuration as described in U.S. Pat. No. 5,304,195 to Twyford et al.

In some applications, other vaso-occlusive devices such as platinum microcoils may be used in combination with the micrografts of the present invention to occlude the aneurysm.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A vascular implant configured for occluding a vasculature of a patient, the vascular implant comprising a tubular textile structure having a distal opening, a metallic core element positioned inside the tubular structure and attached to the tubular structure, the tubular structure formed of a plurality of yarns, and the plurality of yarns are formed from a plurality of filaments, the tubular structure having a first series of peaks defined by the yarns and a first series of valleys formed between the yarns and a second series of peaks and a second series of valleys formed in the tubular structure in a longitudinal direction to create a wavy longitudinally directed shape along a length of the tubular structure.

2. The vascular implant of claim 1, wherein the tubular structure is non-self-expanding along its length from a proximal end to a distal end.

3. The vascular implant of claim 1, wherein the core element has a coiled structure.

4. The vascular implant of claim 1, wherein the tubular structure has an outer diameter less than 0.027 inches.

5. The vascular implant of claim 1, wherein the longitudinal directed shape is a sinusoidal shape.

6. The vascular graft of claim 1, wherein the plurality of filaments have spaces therebetween and the plurality of yarns have spaces therebetween.

7. The vascular graft of claim 1, wherein the vascular implant is shaped in a pre-biased secondary helical shape.

8. The vascular graft of claim 1, wherein a drug is added to an inner diameter of the tubular structure.

9. The vascular graft of claim 1, wherein a drug is infused into a wall of one or more fibers.

10. The vascular graft of claim 1, wherein the vascular graft further comprises a radiopaque marker band, a portion of the radiopaque marker band positioned within the tubular structure and attached to the core element.

11. The vascular graft of claim 10, wherein the marker band is secured to the tubular structure by melting the tubular structure over the marker band.

12. A vascular graft configured for occluding a vasculature of a patient, the vascular graft comprising:
a textile structure forming a tubular structure; and
a core element having a proximal end, a distal end and a lumen within the core element, the core element positioned inside the tubular structure and attached to the tubular structure,
wherein the tubular structure has a distal opening aligned with a longitudinal axis of the vascular graft, the tubular structure includes a braid formed of a plurality of yarns with spaces therebetween and the plurality of yarns are formed by a plurality of fibers, the fibers having spaces therebetween, and the tubular structure has a series of alternating peaks and valleys along a length of a surface of a wall to form a longitudinally extending wavy sinusoidal shape.

13. The vascular graft of claim 12, wherein the vascular graft further comprises a radiopaque marker band, a portion of the radiopaque marker band positioned within the tubular structure.

14. The vascular graft of claim 12, wherein the vascular graft further comprises a radiopaque marker band attached to the core element.

15. The vascular graft of claim 13, wherein the marker band is secured to the tubular structure by melting the tubular structure over the marker band.

16. The vascular graft of claim 13, wherein the vascular graft is movable to a substantially linear configuration for delivery and returns to a non-linear configuration for placement within the vasculature.

17. The vascular graft of claim 12, wherein the core element is made of a radiopaque material and wound into an open pitch helical coil.

18. The vascular graft of claim 12, wherein the braid forms a continuous circumferential wall along a length.

19. The vascular graft of claim 12, wherein the tubular structure has a plurality of peaks defined by the yarns and a plurality of valleys formed between the yarns.

\* \* \* \* \*